United States Patent
Sasikumar et al.

(10) Patent No.: US 12,005,045 B2
(45) Date of Patent: *Jun. 11, 2024

(54) METHOD OF MODULATING TIGIT AND PD-1 SIGNALLING PATHWAYS USING 1,2,4-OXADIAZOLE COMPOUNDS

(71) Applicant: AURIGENE ONCOLOGY LIMITED, Bangalore (IN)

(72) Inventors: Pottayil Govindan Nair Sasikumar, Bangalore (IN); Muralidhara Ramachandra, Bangalore (IN); Seetharamaiah Setty Sudarshan Naremaddepalli, Bangalore (IN); Chennakrishnareddy Gundala, Bangalore (IN)

(73) Assignee: AURIGENE ONCOLOGY LIMITED, Karnataka (IN)

( * ) Notice: Subject to any disclaimer, the term of this patent is extended or adjusted under 35 U.S.C. 154(b) by 0 days.

This patent is subject to a terminal disclaimer.

(21) Appl. No.: 18/518,292

(22) Filed: Nov. 22, 2023

(65) Prior Publication Data

US 2024/0122904 A1    Apr. 18, 2024

Related U.S. Application Data

(63) Continuation of application No. 17/045,916, filed as application No. PCT/IB2019/052039 on Mar. 13, 2019.

(30) Foreign Application Priority Data

Mar. 14, 2018    (IN) .............................. 201841009306

(51) Int. Cl.
*A61K 31/4245*    (2006.01)
*A61P 35/00*    (2006.01)

(52) U.S. Cl.
CPC .......... *A61K 31/4245* (2013.01); *A61P 35/00* (2018.01)

(58) Field of Classification Search
CPC ........................... A61K 31/4245; A61P 35/00
USPC ........................................................ 514/364
See application file for complete search history.

(56) References Cited

U.S. PATENT DOCUMENTS

| | | | | |
|---|---|---|---|---|
| 10,781,189 | B2 * | 9/2020 | Sasikumar | C07D 271/06 |
| 11,465,976 | B2 * | 10/2022 | Sasikumar | A61P 37/02 |
| 11,497,734 | B2 * | 11/2022 | Sasikumar | A61K 31/4245 |
| 2017/0044256 | A1 | 2/2017 | Grogan et al. | |
| 2017/0101386 | A1 | 4/2017 | Sasikumar et al. | |
| 2018/0044303 | A1 | 2/2018 | Sasikumar et al. | |

FOREIGN PATENT DOCUMENTS

| | | |
|---|---|---|
| WO | 2018047143 A1 | 3/2018 |
| WO | 2018073754 A1 | 4/2018 |

OTHER PUBLICATIONS

Johnston et al Cancer Cell, 2014, 26, 923-937 (Year: 2014).*
International Search Report issued in PCT/IB2019/052039, dated Sep. 13, 2019.
Pubchem, Compound Summary for SID 297479174, Available Date: Jan. 27, 2016 (retrieved on Aug. 21, 2019). Retrieved from the Internet: <URL: https://pubchem.ncbi.nlm.nih.gov/substance/297479174> entire document.
Chauvin et al. "TIGIT and PD-1 impair tumor antigen-specific CD8+ T cells in melanoma patients." *The Journal of clinical investigation* 125(5): 2046-2058 (2015).
Furuta et al. "CD271 on melanoma cell is an IFN-γ-inducible immunosuppressive factor that mediates downregulation of melanoma antigens." *Journal of Investigative Dermatology* 134(5): 1369-1377 (2014).
Grogan et al. "TIGIT inhibits CD8+ T cell effector function during chronic viral infection and cancer (TUM7P. 933)." *The Journal of Immunology* 192(1)_Supplement: 203-15 (2014).
Johnston et al. "The immunoreceptor TIGIT regulates antitumor and antiviral CD8+ T cell effector function." *Cancer cell* 26(6): 923-937 (2014).
Joller et al. "Treg cells expressing the coinhibitory molecule TIGIT selectively inhibit proinflammatory Th1 and Th17 cell responses." *Immunity* 40(4): 569-581 (2014).
Lozano et al. "The TIGIT/CD226 axis regulates human T cell function. " *The Journal of Immunology* 188(8): 3869-3875 (2012).
Sarhan et al. "Adaptive NK cells with low TIGIT expression are inherently resistant to myeloid-derived suppressor cells." *Cancer research* 76(19): 5696-5706 (2016).
Stanietsky et al. "The interaction of TIGIT with PVR and PVRL2 inhibits human NK cell cytotoxicity." *Proceedings of the National Academy of Sciences* 106(42): 17858-17863 (2009).
Stanietsky et al. "Mouse TIGIT inhibits NK-cell cytotoxicity upon interaction with PVR." *European journal of immunology* 43(8): 2138-2150 (2013).
Stengel et al. "Structure of TIGIT immunoreceptor bound to poliovirus receptor reveals a cell-cell adhesion and signaling mechanism that requires cis-trans receptor clustering." *Proceedings of the National Academy of Sciences* 109(14): 5399-5404 (2012).

* cited by examiner

*Primary Examiner* — Yevgeny Valenrod
(74) *Attorney, Agent, or Firm* — MEDLER FERRO WOODHOUSE & MILLS PLLC

(57) ABSTRACT

The present invention relates to method of modulating TIGIT signaling pathway and PD-1 signaling pathway. The invention also encompasses the use of the compound of formula (I) or a stereoisomer thereof or a pharmaceutically acceptable salt thereof for the treatment of diseases or disorders mediated by both TIGIT signaling pathway and PD-1 signaling pathway.

19 Claims, 1 Drawing Sheet

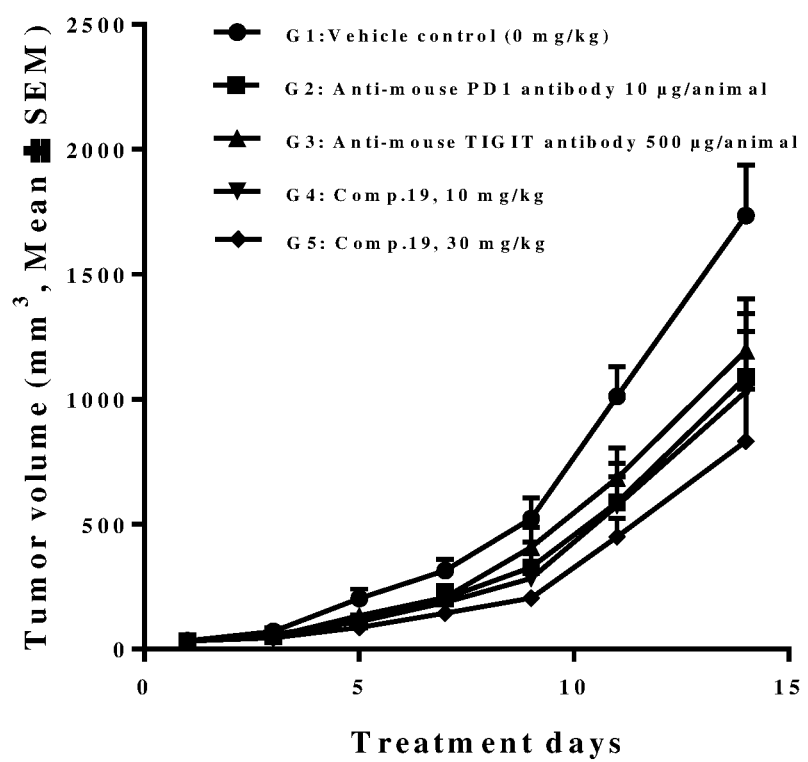

METHOD OF MODULATING TIGIT AND PD-1 SIGNALLING PATHWAYS USING 1,2,4-OXADIAZOLE COMPOUNDS

RELATED APPLICATIONS

This application claims the benefit of Indian provisional application number 201841009306, filed on Mar. 14, 2018; the specifications of which are hereby incorporated by reference in their entirety.

TECHNICAL FIELD

The present invention relates to methods for modulating T cell immunoreceptor with Ig and ITIM domains (TIGIT) and Programmed cell death-1 (PD-1) signaling pathways in a subject comprising administering compound of formula (I) or a pharmaceutically acceptable salt thereof.

BACKGROUND OF THE INVENTION

Immunotherapies that harness the activity of the immune system against tumors are proving to be an effective therapeutic approach in multiple malignancies. Indeed, through accumulation of genetic mutations, many tumors express antigens that can potentially elicit specific tumor immunity. However, tumors can also suppress these responses by activating negative regulatory pathways and checkpoints such as PD-1/PD-L1 and CTLA-4.

TIGIT (T cell immunoreceptor with Ig and ITIM domains) is an inhibitory receptor expressed by activated T cells, Tregs, and NK cells, also known as WUCAM, Vstm3 or Vsig9. TIGIT has an immunoglobulin variable domain, a transmembrane domain, and an immunoreceptor tyrosine-based inhibitory motif (ITIM), and contains signature sequence elements of the PVR protein family. It is known to interact with poliovirus receptor (PVR; CD155) and with nectin2 (CD112) (Stengel et al. (2012) Proc. Nat'l Acad. Sci. (USA) 19:5399). TIGIT suppresses T cell activation by promoting the generation of mature immunoregulatory dendritic cells. TIGIT and other such co-inhibitory molecules (e.g. CTLA-4, PD-1, Lag3 and BTLA) may play a role in evasion of immunosurveillance by tumour cells. Experiments have shown that PVR/CD155 is over-expressed on melanoma cells (Inozume et al. (2014) J. Invest. Dermatol. 134:S121—Abstract 693) and various other tumors. It is possible that the TIGIT/PVR interaction can shield such tumour cells from immune-mediated eradication by inhibiting anti-tumour responses of T and NK cells (Stanietsky et al. (2009) Proc. Nat'l Acad. Sci. (USA) 106:17858 and Lozano et al. (2012) J. Immunol. 188:3869). The TIGIT pathway has been known to negatively regulating NK-cell Function as indicated by reduced killing by either human (Stanietsky et al. (2009) Proc. Nat'l Acad. Sci. (USA); 106:17858) or mouse (Stanietsky et al. (2013) Eur J Immunol. 43:2138) primary NK cells due to CD155/TIGIT interaction. Additionally, MDSC-induced suppression of NK-cell function (degranulation, IFN-7 production) was shown to be dependent on CD155-TIGIT interaction and greater functional suppression observed by TIGIThigh NK cells (Sarhan et al. (2016) Cancer Res 2016; 76:5696). Other experiments have identified a TIGIT subset of regulatory T cells (Tregs) that selectively suppress Th1 and Th17 responses (Joller et al. (2014) Immunity 40:569), suggesting an alternative mechanism by which TIGIT-blocking agents may enhance anti-tumour immune response.

TIGIT may act to 'turn off' the immune response similarly to other co-inhibitory receptors such as CTLA-4, PD-1 and BTLA. Antibodies targeting CTLA-4 (ipilimumab) and PD-1 (nivolumab, pembrolizumab) have been approved for the treatment of human cancers, validating this therapeutic approach. Antibodies or other agents that bind to human TIGIT might also find use in treatment of cancers. In mouse models, antibody blockade of both PD-L1 and TIGIT leads to a synergistic enhancement of CD8<+> T cell mediated tumour rejection (Grogan et al. (2014) J. Immunol. 192(1) Suppl. 203.15; Johnston et al. (2014) Cancer Cell 26:1-15). Similar results have been obtained in animal models of melanoma (Inozume et al. (2014) J. Invest. Dermatol. 134: S121—Abstract 693).

Some experiments suggest that TIGIT blockade is effective to enhance anti-tumour CD8<+> T cell response only in the presence of the co-activating receptor DNAM-1/CD226, which competes with TIGIT for binding to PVR/CD155 (Johnston et al. (2014) Cancer Cell 26:1-15). Further experiments have explained that mAbs (monoclonal antibodies) acting for dual TIGIT and PD-1 blockade enhance CD8+ T cell responses to melanoma and improve the clinical efficacy of PD-1 blockade for patients with advanced melanoma (Joe-Marc Chauvin et al., (2015), J Clin Invest. May 1; 125(5): 2046-2058).

Thus, in view of the fact that the use of TIGIT blockade in combination with PD-1 blockade in potentiating immune related diseases such as cancers is not explored much, there is an unmet need exists to develop potent therapeutic agents that exhibit dual inhibition of TIGIT and PD-1 signaling pathway.

SUMMARY OF THE INVENTION

The present invention relates to methods of modulating T cell immunoreceptor with Ig and ITIM domains (TIGIT) signaling pathway and programmed cell death 1 (PD-1) signaling pathway using 1,2,4-oxadiazole compounds or a stereoisomer thereof or a pharmaceutically acceptable salt thereof.

In one aspect, the present disclosure provides a method of modulating T cell immunoreceptor with Ig and ITIM domains (TIGIT) signaling pathway and programmed cell death 1 (PD-1) signaling pathway in a subject, comprising contacting the subject with compound of formula (I), or a stereoisomer thereof or a pharmaceutically acceptable salt thereof:

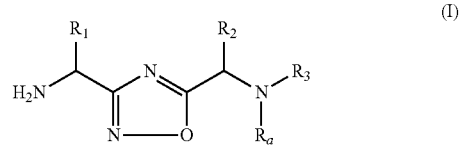

wherein,
R$_1$ represents hydrogen, —(C$_1$-C$_6$)alkyl optionally substituted with —OH, —COOH, aryl, heteroaryl, or aryl-OH;
R$_2$ represents hydrogen, —(C$_1$-C$_6$)alkyl optionally substituted with —OH, —SH, C(O)NH$_2$, —COOH, aryl, heteroaryl, or aryl-OH;
R$_a$ represents hydrogen; or R$_a$ and R$_2$ taken together with the atom to which they are attached form a pyrrolidine ring;

R₃ represents hydrogen or a group represented by formula (I'),

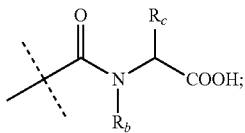

(I')

---- represents point of attachment;
R_b represents hydrogen; or R_b and R_c taken together with the atoms to which they are attached form a pyrrolidine ring;
R_c represents hydrogen, —(C₁-C₆)alkyl optionally substituted with —OH, —C(O)NH₂, COOH, aryl, or aryl-OH.

BRIEF DESCRIPTION OF FIGURE

FIG. 1: Antitumor effect of Compound 19 in CT26 tumor bearing mice

DETAILED DESCRIPTION OF THE INVENTION

The present invention provides a method of modulating TIGIT signaling pathway and PD-1 signaling pathways using 1,2,4-oxadiazole compounds or a stereoisomer thereof or a pharmaceutically acceptable salt thereof. This invention also provides a method for treatment of diseases or disorders mediated by both TIGIT and PD-1 comprising administering a compound of formula (I), or a stereoisomer thereof or a pharmaceutically acceptable salt thereof.

Each embodiment is provided by way of explanation of the invention, and not by way of limitation of the invention. In fact, it will be apparent to those skilled in the art that various modification and variations can be made in the present invention without departing from the scope or spirit of the invention. For instance, features illustrated or described as part of one embodiment can be used on another embodiment to yield a still further embodiment. Thus it is intended that the present invention cover such modifications and variations as come within the scope of the appended claims and their equivalents. Other objects, features, and aspects of the present invention are disclosed in, or are obvious from, the following detailed description. It is to be understood by one of ordinary skill in the art that the present discussion is a description of exemplary embodiments only, and is not to be construed as limiting the broader aspects of the present invention.

In certain embodiments, the present invention provides a method of modulating T cell immunoreceptor with Ig and ITIM domains (TIGIT) signaling pathway and programmed cell death 1 (PD-1) signaling pathway in a subject, comprising contacting the subject with compound of formula (I), or a stereoisomer thereof or a pharmaceutically acceptable salt thereof:

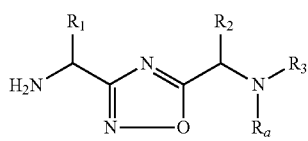

(I)

wherein,
R₁ represents hydrogen, —(C₁-C₆)alkyl optionally substituted with —OH, —COOH, aryl, heteroaryl, or aryl-OH;
R₂ represents hydrogen, —(C₁-C₆)alkyl optionally substituted with —OH, —SH, C(O)NH₂, —COOH, aryl, heteroaryl, or aryl-OH;
R_a represents hydrogen; or R_a and R₂ taken together with the atom to which they are attached form a pyrrolidine ring;
R₃ represents hydrogen or a group represented by formula (I'),

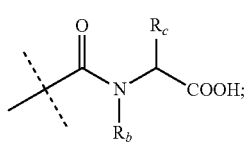

(I')

---- represents point of attachment;
R_b represents hydrogen; or R_b and R_c taken together with the atoms to which they are attached form a pyrrolidine ring;
R_c represents hydrogen, —(C₁-C₆)alkyl optionally substituted with —OH, —C(O)NH₂, COOH, aryl, or aryl-OH.

In certain embodiments, R₁ represents hydrogen, —(C₁-C₆)alkyl optionally substituted with —OH, —COOH, phenyl, imidazolyl, or (p-OH)phenyl.

In certain embodiments, R₁ represents —(C₁-C₆)alkyl optionally substituted with —OH, —COOH, imidazolyl, phenyl, or (p-OH)phenyl.

In certain embodiments, R₁ represents —(C₁-C₆)alkyl optionally substituted with —OH, —COOH, imidazolyl, or (p-OH)phenyl.

In certain embodiments, R₂ represents hydrogen, —(C₁-C₆)alkyl optionally substituted with —OH, —SH, —C(O)NH₂, —COOH, phenyl, imidazolyl, or (p-OH)phenyl.

In certain embodiments, R₂ represents hydrogen, —(C₁-C₆)alkyl optionally substituted with —C(O)NH₂, phenyl, or (p-OH)phenyl.

In certain embodiments, R₂ represents hydrogen, —(C₁-C₆)alkyl substituted with —OH, —SH, —COOH, phenyl, imidazolyl, or (p-OH)phenyl.

In certain embodiments, R₂ represents hydrogen, —(C₁-C₆)alkyl substituted with —OH, —COOH, phenyl, imidazolyl, or (p-OH)phenyl.

In certain embodiments, R_a represents hydrogen.
In certain embodiments, R_a and R₂ taken together with the atom to which they are attached form a pyrrolidine ring.
In certain embodiments, R₃ represents

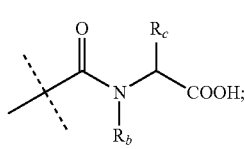

(I')

wherein
---- represents point of attachment;
R_b represents hydrogen; or R_b and R_c taken together with the atoms to which they are attached form a pyrrolidine ring;

$R_c$ represents hydrogen, —($C_1$-$C_6$)alkyl optionally substituted with —OH, —C(O)$NH_2$, COOH, phenyl, or (p-OH)phenyl.

In certain embodiments, $R_b$ and $R_c$ taken together with the atoms to which they are attached form a pyrrolidine ring.

In certain embodiments, the compounds described in the present invention is represented by compound of formula (IA),

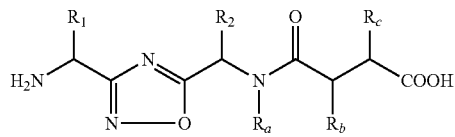

(IA)

wherein, $R_1$, $R_2$, $R_a$, $R_b$, and $R_c$ are as defined in compound of formula (I).

In certain embodiments, the compounds described in the present invention is represented by compound of formula (IA), or a stereoisomer thereof or a pharmaceutically acceptable salt thereof: wherein
  $R_1$ represents —($C_1$-$C_6$)alkyl optionally substituted with —OH, —COOH, imidazolyl, phenyl, or (p-OH)phenyl;
  $R_2$ represents hydrogen, —($C_1$-$C_6$)alkyl substituted with —OH, —SH, —COOH, phenyl, imidazolyl, or (p-OH)phenyl;
  $R_a$ represents hydrogen; or $R_a$ and $R_2$ taken together with the atom to which they are attached form a pyrrolidine ring;
  $R_b$ represents hydrogen; or $R_b$ and $R_c$ taken together with the atoms to which they are attached form a pyrrolidine ring; and
  $R_c$ represents hydrogen, —($C_1$-$C_6$)alkyl optionally substituted with —OH, —C(O)$NH_2$, —COOH, phenyl, or (p-OH)phenyl.

In certain embodiments, the compounds described in the present invention is represented by compound of formula (IA), or a stereoisomer thereof or a pharmaceutically acceptable salt thereof: wherein $R_1$ represents —($C_1$-$C_6$)alkyl optionally substituted with —OH, —COOH, imidazolyl, or (p-OH)phenyl; and $R_2$ represents hydrogen, —($C_1$-$C_6$)alkyl substituted with —OH, —COOH, phenyl, imidazolyl, or (p-OH)phenyl.

In certain embodiments, the compounds described in the present invention is represented by compound of formula (IB), (IB)

wherein, $R_1$, $R_2$ and $R_a$, are as defined in compound of formula (I).

In certain embodiments, the compounds described in the present invention is represented by compound of formula (IB), or a stereoisomer thereof or a pharmaceutically acceptable salt thereof: wherein
  $R_1$ represents —($C_1$-$C_6$)alkyl optionally substituted with —OH or (p-OH)phenyl;
  $R_2$ represents hydrogen, —($C_1$-$C_6$)alkyl substituted with phenyl or (p-OH)phenyl; and
  $R_a$ and $R_2$ taken together with the atom to which they are attached form a pyrrolidine ring.

In certain embodiments, the term 'aryl' indicates phenyl.

In certain embodiments, the term 'heteroaryl' indicates imidazole.

In certain embodiments, the dual modulators of TIGIT signalling pathway and PD-1 signalling pathway is compound of formula (I):

(I)

wherein,
  $R_1$ represents hydrogen, —($C_1$-$C_6$)alkyl optionally substituted with —OH, COOH, aryl, heteroaryl, or aryl-OH;
  $R_2$ represents hydrogen, —($C_1$-$C_6$)alkyl optionally substituted with —OH, —SH, C(O)$NH_2$, —COOH, aryl, heteroaryl, or aryl-OH;
  $R_a$ represents hydrogen; or $R_a$ and $R_2$ taken together with the atom to which they are attached form a pyrrolidine ring;
  $R_3$ represents hydrogen or a group represented by formula (I'), (I')

---- represents point of attachment to —N—$R_a$ group;
  $R_b$ represents hydrogen; or $R_b$ and $R_c$ taken together with the atoms to which they are attached form a pyrrolidine ring;
  $R_c$ represents hydrogen, —($C_1$-$C_6$)alkyl substituted with —OH, —C(O)$NH_2$, —COOH, aryl, or aryl-OH.

In certain embodiments, the present invention provides a method of modulating T cell immunoreceptor with Ig and ITIM domains (TIGIT) signaling pathway and programmed cell death 1 (PD-1) signaling pathway in a subject, comprising contacting the subject with compound of formula (I), or a stereoisomer thereof or a pharmaceutically acceptable salt thereof:

(I)

$R_1$ represents hydrogen, —$CH_2$-aryl-OH, —$CH_2$—COOH, —$CH_2$-imidazolyl, —($CH_2$)$_2$—COOH, —CH($CH_3$)$_2$, —$CH_2$-aryl, —CH($CH_3$)OH, or —$CH_2$(CH)($CH_3$)$_2$;

R$_2$ represents hydrogen, —CH(CH$_3$)OH, —CH$_2$-aryl-OH, —CH$_2$—SH, —CH$_2$-imidazolyl, —CH(CH$_3$)$_2$, —(CH$_2$)$_2$—COOH, —(CH$_2$)$_2$—CONH$_2$, or —CH$_2$-aryl;

R$_a$ represents hydrogen; or R$_a$ and R$_2$ taken together with the atom to which they are attached form a pyrrolidine ring;

R$_3$ represents hydrogen or a group represented by formula (I'),

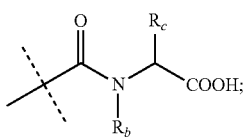

(I')

---- represents point of attachment to —N—R$_a$ group;

R$_b$ represents hydrogen; or R$_b$ and R$_c$ taken together with the atoms to which they are attached form a pyrrolidine ring;

R$_c$ represents hydrogen, —CH$_2$—COOH, —CH(CH$_3$)OH, —CH$_2$-aryl-OH, —CH$_2$-aryl, —(CH$_2$)$_2$—CONH$_2$, or —CH(CH$_3$)CH$_2$CH$_3$.

In certain embodiments, R$_1$ represents hydrogen or —CH(CH$_3$)OH.

In certain embodiments, R$_2$ represents —(CH$_2$)$_2$—COOH.

In certain embodiments, the present invention provides a method of modulating T cell immunoreceptor with Ig and ITIM domains (TIGIT) signaling pathway and programmed cell death 1 (PD-1) signaling pathway in a subject, comprising contacting the subject with compound of formula (I), or a stereoisomer thereof or a pharmaceutically acceptable salt thereof: wherein the compound is:

| Compound No. | Structure |
|---|---|
| 1 | 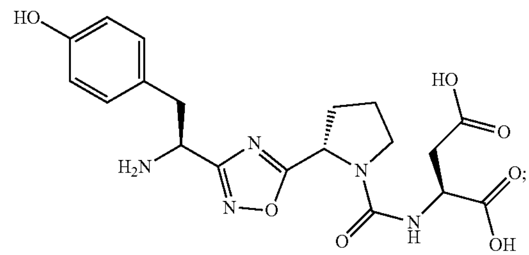 [SMILES: N[C@@H](Cc1ccc(O)cc1)c1noc([C@@H]2CCCN2C(=O)N[C@@H](CC(=O)O)C(=O)O)n1] |
| 2 | 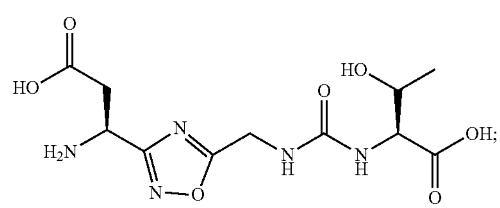 [SMILES: CC(O)[C@H](NC(=O)NCc1nc([C@@H](N)CC(=O)O)no1)C(=O)O] |
| 3 | 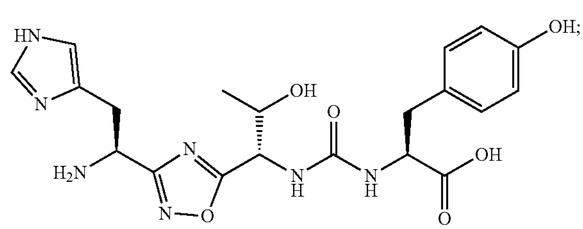 [SMILES: CC(O)[C@H](NC(=O)N[C@@H](Cc1ccc(O)cc1)C(=O)O)c1nc([C@@H](N)Cc2c[nH]cn2)no1] |
| 4 | 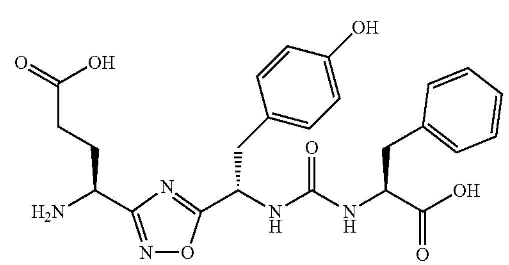 |

-continued

| Compound No. | Structure |
|---|---|
| 5 | *structure* |
| 6 | *structure* |
| 7 | *structure* |
| 8 | *structure* |
| 9 | *structure* |
| 10 | *structure* |
| 11 | *structure* |

-continued
| Compound No. | Structure |
|---|---|
| 12 | 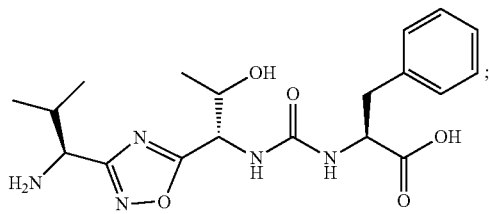 [SMILES: CC(C)[C@H](N)c1noc([C@@H](NC(=O)N[C@@H](Cc2ccccc2)C(=O)O)C(C)O)n1] |
| 13 | 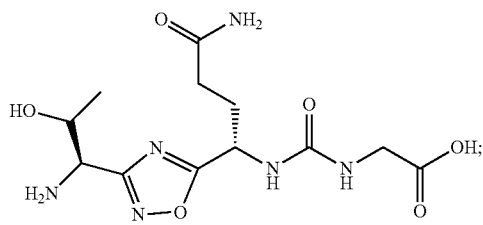 [SMILES: CC(O)[C@H](N)c1noc([C@H](CCC(N)=O)NC(=O)NCC(=O)O)n1] |
| 14 | 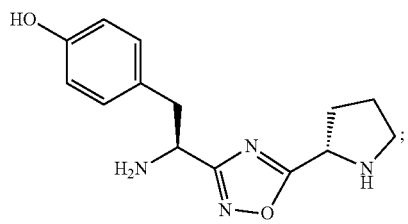 [SMILES: N[C@@H](Cc1ccc(O)cc1)c1noc([C@@H]2CCCN2)n1] |
| 15 | 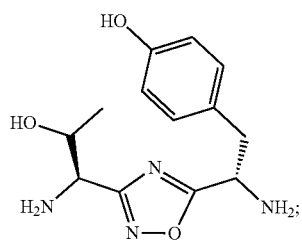 [SMILES: CC(O)[C@H](N)c1noc([C@@H](N)Cc2ccc(O)cc2)n1] |
| 16 | 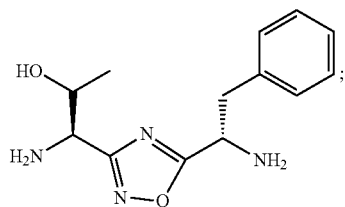 [SMILES: CC(O)[C@H](N)c1noc([C@@H](N)Cc2ccccc2)n1] |
| 17 | 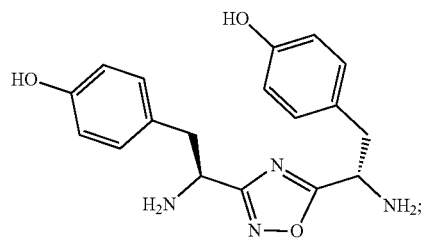 [SMILES: N[C@@H](Cc1ccc(O)cc1)c1noc([C@@H](N)Cc2ccc(O)cc2)n1] |

| Compound No. | Structure |
|---|---|
| 18 | (structure) |
| 19 | (structure) |
| 20 | (structure) | or a pharmaceutically acceptable salt or a stereoisomer thereof.

In certain embodiments, the present invention provides a method of modulating T cell immunoreceptor with Ig and ITIM domains (TIGIT) signaling pathway and programmed cell death 1 (PD-1) signaling pathway in a subject, comprising contacting the subject with compound of formula (I), or a stereoisomer thereof or a pharmaceutically acceptable salt thereof: wherein the compound is:

| Compound No. | Structure |
|---|---|
| 1 | (structure) |
| 2 | (structure) |

-continued
| Compound No. | Structure |
|---|---|
| 3 | 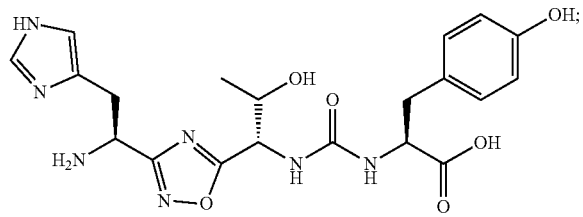 [SMILES: CC(O)[C@H](NC(=O)N[C@@H](Cc1ccc(O)cc1)C(=O)O)c1nc([C@@H](N)Cc2c[nH]cn2)no1] |
| 4 | 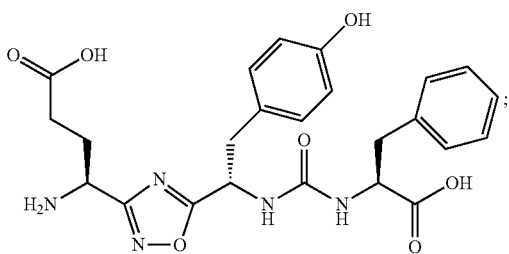 [SMILES: N[C@@H](CCC(=O)O)c1noc([C@H](Cc2ccc(O)cc2)NC(=O)N[C@@H](Cc2ccccc2)C(=O)O)n1] |
| 5 | 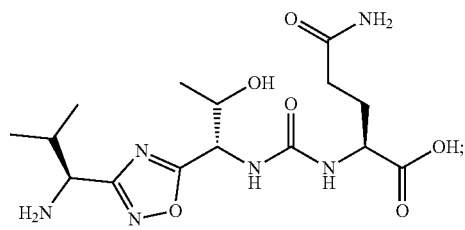 [SMILES: CC(C)[C@H](N)c1noc([C@@H](NC(=O)N[C@@H](CCC(N)=O)C(=O)O)C(C)O)n1] |
| 6 | 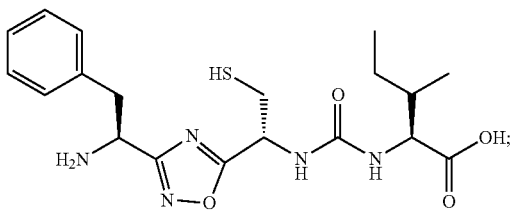 [SMILES: CCC(C)[C@H](NC(=O)N[C@@H](CS)c1nc([C@@H](N)Cc2ccccc2)no1)C(=O)O] |
| 7 | 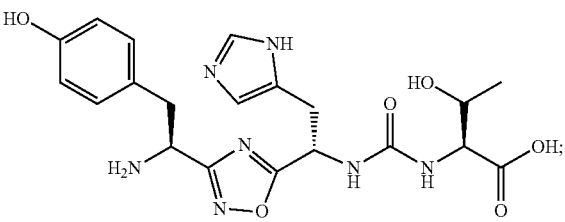 [SMILES: CC(O)[C@H](NC(=O)N[C@@H](Cc1cnc[nH]1)c1nc([C@@H](N)Cc2ccc(O)cc2)no1)C(=O)O] |
| 14 | 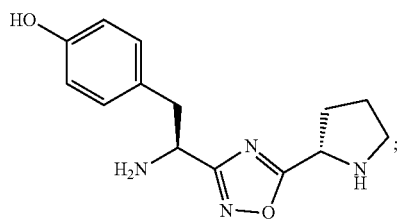 [SMILES: N[C@@H](Cc1ccc(O)cc1)c1noc([C@@H]2CCCN2)n1] |

| Compound No. | Structure |
|---|---|
| 19 | 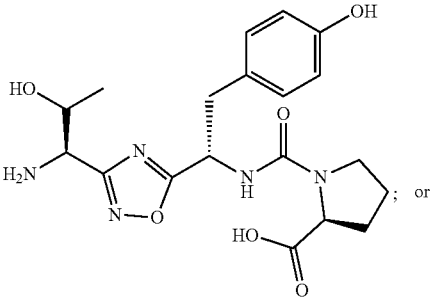 [SMILES: CC(O)[C@H](N)c1noc([C@H](Cc2ccc(O)cc2)NC(=O)N2CCC[C@H]2C(=O)O)n1] ; or |
| 20 | 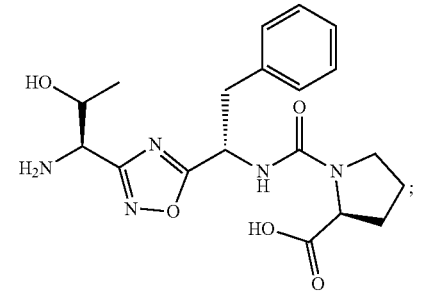 [SMILES: CC(O)[C@H](N)c1noc([C@H](Cc2ccccc2)NC(=O)N2CCC[C@H]2C(=O)O)n1] ; | or a pharmaceutically acceptable salt thereof.

In certain embodiments, compounds of the invention may be prodrugs of the compounds of formula (I), e.g., wherein a hydroxyl in the parent compound is presented as an ester or a carbonate or carboxylic acid present in the parent compound is presented as an ester. In a further embodiment, the prodrug is metabolized to the active parent compound in vivo (e.g., the ester is hydrolyzed to the corresponding hydroxyl or carboxylic acid).

In certain embodiments, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention and their uses. Exemplary isotopes that can be incorporated in to compounds of the invention include isotopes of hydrogen, carbon, nitrogen, oxygen, phosphorous, sulfur, fluorine, chlorine and iodine, such as $^2H$ ("D"), $^3H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$ and $^{125}I$. Isotopically labeled compounds of the present inventions can generally be prepared by following procedures analogous to those disclosed in the schemes and/or in the examples herein below, by substituting an isotopically labeled reagent for a non-isotopically labeled reagent.

The methods of the present invention may be utilized to treat a subject in need thereof. In certain embodiments, the individual is a mammal such as a human or a non-human mammal. When administered to an animal, such as a human, the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the present disclosure provides a method of modulating T cell immunoreceptor with Ig and ITIM domains (TIGIT) signaling pathway and programmed cell death 1 (PD-1) signaling pathway (e.g., PD-1, PD-L1, or PD-L2) in a subject, comprising contacting the subject with compound of formula (I), or a stereoisomer thereof or a pharmaceutically acceptable salt thereof, according to any of the above embodiments.

In certain embodiments, the present disclosure provides a method of modulating T cell immunoreceptor with Ig and ITIM domains (TIGIT) signaling pathway comprising contacting the subject with compound 19 disclosed herein or a stereoisomer thereof or a pharmaceutically acceptable salt thereof.

In certain embodiments, the present disclosure provides a method of modulating T cell immunoreceptor with Ig and ITIM domains (TIGIT) signaling pathway comprising contacting the subject with compound 20 disclosed herein or a stereoisomer thereof or a pharmaceutically acceptable salt thereof.

In accordance with any of the foregoing embodiments, in certain embodiments, contacting the cell occurs in a subject in need thereof, thereby treating a disease or disorder selected from cancer, immune disorders, immunodeficiency disorders, inflammatory disorders, infectious diseases, and transplant rejection.

In certain embodiments, the disease or disorder is cancer.

In certain embodiments, the present disclosure provides method for inhibiting growth of tumor cells and/or metastasis comprising administering a therapeutically effective amount to the subject in need thereof a TIGIT/PD-1 dual pathway inhibitor.

In certain embodiments, the tumor cells are from a cancer selected from small cell lung cancer, multiple myeloma, bladder carcinoma, primary ductal carcinoma, ovarian carcinoma, Hodgkin's lymphoma, gastric carcinoma, acute myeloid leukemia, and pancreatic cancer.

In certain embodiments, the tumor cells are from a cancer selected from blastoma, breast cancer, epithelial cancer, colon cancer, lung cancer, melanoma, prostate cancer, renal cancer, bone cancer, pancreatic cancer, skin cancer, cancer of the head or neck, uterine cancer, ovarian cancer, colorectal cancer, rectal cancer, cancer of the anal region, cancer of the peritoneum, stomach cancer, testicular cancer, carcinoma of the fallopian tubes, carcinoma of the endometrium, cervical cancer, vaginal cancer, vulval cancer, cancer of the esophagus, cancer of the small intestine, cancer of the endocrine system, cancer of the thyroid gland, cancer of the parathyroid gland, cancer of the adrenal gland, sarcoma, cancer of the urethra, cancer of the penis, chronic or acute leukemia, solid tumors of childhood, Hodgkin's lymphoma, non-Hodgkin's lymphoma, cutaneous T cell lymphoma, mesothelioma, thymic carcinoma, myeloma, cancer of the bladder, cancer of the ureter, carcinoma of the renal pelvis, liver cancer, pancreatic cancer, post-transplant lymphoproliferative disorder (PTLD), neoplasm of the central nervous system (CNS), tumor angiogenesis, spinal axis tumor, brain stem glioma, pituitary adenoma, epidermoid cancer, salivary gland carcinoma, squamous cell cancer, abnormal vascular proliferation associated with phakomatoses, edema (such as that associated with brain tumors), Meigs' syndrome, Merkel cell carcinoma, and environmentally induced cancers.

In certain embodiments, the present invention provides a method for inhibiting growth of tumor cells and/or metastasis in a subject, comprising administering to the subject in need thereof a TIGIT/PD-1 dual pathway inhibitor.

In certain embodiments, the tumor cells are of a cancer selected from small cell lung cancer, multiple myeloma, bladder carcinoma, primary ductal carcinoma, ovarian carcinoma, Hodgkin's lymphoma, gastric carcinoma, acute myeloid leukemia, and pancreatic cancer.

In certain embodiments, the tumor cells are of a cancer selected from blastoma, breast cancer, epithelial cancer, colon cancer, lung cancer, melanoma, prostate cancer, renal cancer, bone cancer, pancreatic cancer, skin cancer, cancer of the head or neck, uterine cancer, ovarian cancer, colorectal cancer, rectal cancer, cancer of the anal region, cancer of the peritoneum, stomach cancer, testicular cancer, carcinoma of the fallopian tubes, carcinoma of the endometrium, cervical cancer, vaginal cancer, vulval cancer, cancer of the esophagus, cancer of the small intestine, cancer of the endocrine system, cancer of the thyroid gland, cancer of the parathyroid gland, cancer of the adrenal gland, sarcoma, cancer of the urethra, cancer of the penis, chronic or acute leukemia, solid tumors of childhood, Hodgkin's lymphoma, non-Hodgkin's lymphoma, cutaneous T cell lymphoma, mesothelioma, thymic carcinoma, myeloma, cancer of the bladder, cancer of the ureter, carcinoma of the renal pelvis, liver cancer, pancreatic cancer, post-transplant lymphoproliferative disorder (PTLD), neoplasm of the central nervous system (CNS), tumor angiogenesis, spinal axis tumor, brain stem glioma, pituitary adenoma, epidermoid cancer, salivary gland carcinoma, squamous cell cancer, abnormal vascular proliferation associated with phakomatoses, edema (such as that associated with brain tumors), Meigs' syndrome, Merkel cell carcinoma, and environmentally induced cancers.

In certain embodiments, the present invention provides methods for treating cancer, wherein the method comprises administration to the subject in need thereof a TIGIT/PD-1 dual pathway inhibitor.

In accordance with any of the foregoing embodiments, in certain embodiments, TIGIT/PD-1 dual pathway inhibitor is compound of formula (I) or a stereoisomer thereof or a pharmaceutically acceptable salts thereof.

In accordance with any of the foregoing embodiments, in certain embodiments, TIGIT/PD-1 dual pathway inhibitor is compound of formula (IA) or a stereoisomer thereof or a pharmaceutically acceptable salts thereof.

In accordance with any of the foregoing embodiments, in certain embodiments, TIGIT/PD-1 dual pathway inhibitor is compound of formula (IB) or a stereoisomer thereof or a pharmaceutically acceptable salts thereof.

In certain embodiments, the present invention provides methods for treating cancer, mediated by TIGIT, wherein the method comprises administration to the subject in need thereof compound 19 or 20, or a stereoisomer thereof or a pharmaceutically acceptable salt thereof.

In certain embodiments, the present invention provides methods for inhibiting growth of tumor cells and/or metastasis in a subject, comprising administering to the subject in need thereof, the compound of formula (I) or a pharmaceutically acceptable salts, capable of inhibiting the T cell immunoreceptor with Ig and ITIM domains (TIGIT) pathway and programmed cell death 1 (PD1) signaling pathway.

In certain embodiments, the present invention provides methods for inhibiting growth of tumor cells and/or metastasis in a subject, comprising administering to the subject in need thereof, the compound of formula (IA) or a pharmaceutically acceptable salts, capable of inhibiting the T cell immunoreceptor with Ig and ITIM domains (TIGIT) pathway and programmed cell death 1 (PD1) signaling pathway.

In certain embodiments, the present invention provides methods for inhibiting growth of tumor cells and/or metastasis in a subject, comprising administering to the subject in need thereof, the compound of formula (IB) or a pharmaceutically acceptable salts, capable of inhibiting the T cell immunoreceptor with Ig and ITIM domains (TIGIT) pathway and programmed cell death 1 (PD1) signaling pathway.

In view of the upregulation of TIGIT on CD8+ T cells upon activation (Joller et al. (2011) J Immunol. 186:1338), a large number of cancer indications are expected to respond to TIGIT-blocking agents. Available data also indicate high level of expression of TIGIT on CD8+ TILs in non-small cell lung cancer, colon cancer, and melanoma (Chauvin et al. (2015) Clin Investig. 125:2046; Johnston et al. (2014) Cancer Cell. 26:923), on T cells in chronic lymphocytic leukemia (Catakovic et al., (2017) Oncoimmunology 7(1): e1371399) and follicular lymphoma (Josefsson et al. (2018) Clin Cancer Res. 24:870) and in the peripheral blood mononuclear cells (PBMCs) of acute myelogenous leukemia (AML) patients (Kong et al. (2016) Clin Cancer Res. 22:3057).

Representative tumor cells disclosed therein include cells of a cancer such as, but not limited to, blastoma (e.g., glioblastoma), breast cancer (e.g., breast carcinoma, primary ductal carcinoma, triple negative breast cancer, estrogen receptor positive (ER+), progesterone receptor positive (PR+), and/or human epidermal growth factor receptor 2 positive (HER2+)), epithelial cancer (e.g., carcinomas), colon cancer, lung cancer (e.g., small cell lung cancer, non-small cell lung cancer (NSCLC), lung adenocarcinoma, and lung squamous cell carcinoma), melanoma (e.g., cutaneous melanoma, ocular melanoma, cutaneous or intraocular malignant melanoma, and lymph node-associated melanoma), prostate cancer (e.g., prostate adenocarcinoma), renal cancer (e.g., renal cell cancer (RCC) and kidney cancer), bone cancer (e.g., osteosarcoma), pancreatic cancer (e.g., pancreatic adenocarcinoma), skin cancer, cancer of the head or neck (e.g., head and neck squamous cell carcinoma), uterine cancer, ovarian cancer (e.g., ovarian carcinoma), colorectal cancer (e.g., microsatellite instability high colorectal cancer and colorectal adenocarcinoma), rectal cancer, cancer of the anal region, cancer of the peritoneum, stomach cancer (e.g., gastric carcinoma and gastrointestinal cancer), testicular cancer, carcinoma of the fallopian tubes, carcinoma of the endometrium, cervical cancer (e.g., carcinoma of the cervix), vaginal cancer (e.g., carcinoma of the vagina), vulval cancer (e.g., carcinoma of the vulva), cancer of the esophagus, cancer of the small intestine, cancer of the endocrine system, thyroid cancer (e.g., cancer of the thyroid gland), cancer of the parathyroid gland, cancer of the adrenal gland, sarcoma (e.g., sarcoma of soft tissue and Kaposi's sarcoma), cancer of the urethra, cancer of the penis, chronic or acute leukemia, (e.g., acute myeloid leukemia, chronic myeloid leukemia, acute lymphoblastic leukemia, chronic lymphocytic leukemia, Hairy cell leukemia, and chronic myeloblastic leukemia), solid tumors of childhood, Hodgkin's lymphoma (HL) (e.g., lymphocyte-rich (LRCHL), nodular sclerosis (NSHL), mixed cellularity (MCHL) and lymphocyte depleted (LDHL)), B-cell lymphomas (e.g., diffuse large B-cell lymphoma (DLBCL)), non-Hodgkin's lymphoma (NHL) (e.g., low grade/follicular non-Hodgkin's lymphoma, small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, Burkitt's lymphoma, mantle cell lymphoma), AIDS-related lymphoma, cutaneous T-cell lymphoma (e.g., mycosis fundoides) and Waldenstrom's Macroglobulinemia, post-transplant lymphoproliferative disorder (PTLD), lymphocytic lymphoma, primary CNS lymphoma, and T-cell lymphoma), mesothelioma, thymic carcinoma, myeloma (e.g., multiple myeloma), cancer of the bladder (e.g., bladder carcinoma), cancer of the ureter, carcinoma of the renal pelvis, liver cancer (e.g., hepatocellular cancer, hepatic carcinoma, hepatoma), pancreatic cancer, post-transplant lymphoproliferative disorder (PTLD), neoplasm of the central nervous system (CNS), tumor angiogenesis, spinal axis tumor, brain stem glioma, pituitary adenoma, epidermoid cancer, salivary gland carcinoma, squamous cell cancer, abnormal vascular proliferation associated with phakomatoses, edema (such as that associated with brain tumors), Meigs' syndrome, Merkel cell carcinoma, environmentally induced cancers (including those induced by asbestos), and combinations of said cancers.

In other embodiments, for example, the tumor cells may include cells of a cancer selected from prostate cancer, melanoma, breast cancer, colon cancer, prostate cancer, lung cancer, renal cancer, pancreatic cancer, gastric carcinoma, bladder cancer, esophageal cancer, mesothelioma, thyroid cancer, thymic carcinoma, sarcoma, glioblastoma, chronic or acute leukemia, lymphoma, myeloma, Merkel cell carcinoma, epithelial cancer, colorectal cancer, vaginal cancer, cervical cancer, ovarian cancer, and cancer of the head and neck.

In other embodiments, for example, the tumor cells may include cells of a cancer selected from melanoma, triple negative breast cancer, non-small cell lung cancer, renal cell carcinoma, pancreatic cancer, gastric carcinoma, bladder cancer, mesothelioma, Hodgkins's lymphoma, cervical cancer, ovarian cancer, and head and neck squamous cell carcinoma. In other embodiments, for example, the tumor cells may include cells of a cancer selected from prostate cancer, melanoma, breast cancer, colon cancer, prostate cancer, lung cancer, renal cancer, pancreatic cancer, gastric carcinoma, bladder cancer, esophageal cancer, mesothelioma, thyroid cancer, thymic carcinoma, sarcoma, glioblastoma, chronic or acute leukemia, lymphoma, myeloma, Merkel cell carcinoma, epithelial cancer, colorectal cancer, vaginal cancer, cervical cancer, ovarian cancer, and cancer of the head and neck.

In other embodiments, for example, the tumor cells may include cells of a cancer selected from melanoma, triple negative breast cancer, non-small cell lung cancer, renal cell carcinoma, pancreatic cancer, gastric carcinoma, bladder cancer, mesothelioma, Hodgkins's lymphoma, cervical cancer, ovarian cancer, and head and neck squamous cell carcinoma.

In some embodiments, the tumor cells are, and/or the subject is, naïve to immunooncology therapy. Immunooncology uses the subject's immune system to help fight cancer. For example, an immunooncology therapy includes, but is not limited to, atezolizumab (human monoclonal antibody that targets PD-L1), avelumab (human monoclonal antibody that targets PD-L1), brentuximab vedotin (antibody-drug conjugate that targets CD30), rituximab (antibody that targets CD20), durvalamab (human monocle`onal antibody that targets PD-L1), ipilimumab (human monoclonal antibody that targets CTLA-4), nivolumab (human monoclonal antibody that targets PD-L1), pembrolizumab (also referred to as lambrolizumab, human monoclonal antibody that targets PD-L1), tremelimumab (human monoclonal antibody that targets CTLA-4), CT-011 (antibody that targets PD-1), MDX-1106 (antibody that targets PD-1), MK-3475 (antibody that targets PD-1), YW243.55.S70 (antibody that targets PD-L1), MPDL3280A (antibody that targets PD-L1), MDX-1105 (antibody that targets PD-L1), and MEDI4736 (antibody that targets PD-L1). In some embodiments, the immunooncology therapy is selected from an anti-CTLA-4 antibody, an anti-PD-1 antibody, an anti-PD-L1 antibody, an anti-PD-L2 antibody, an anti-TIGIT antibody (e.g., antibodies disclosed in WO 2015/009856).

In further embodiments, the present disclosure provide a method of treatment of infection by blockade of the TIGIT signaling pathway and PD-1 signalling pathway, for example inhibiting an immunosuppressive signal induced by PD-1, (e.g., PD-1, PD-L1, or PD-L2) and TIGIT, wherein the method comprises administration of a therapeutically effective amount of a compound of Formula (I) to the subject in need thereof.

In some embodiments, the infectious disease is a bacterial infection, a viral infection, a fungal infection, or a parasitic infection, as well as methods of administering a therapeutically effective amount of a compound of Formula (I) for the treatment of a bacterial infection, a viral infection, a fungal infection, or a parasitic infection.

In view of the upregulation of TIGIT on CD8+ T cells upon activation (Joller et al. (2011) J Immunol. 186:1338) TIGIT-blocking agents are expected to be effective in a larger number of infectious diseases. TIGIT has been reported to enforce CD8+ T cell exhaustion in chronic infections caused by LCMV (Johnston et al. (2014) Cancer Cell. 26) and HIV (Tauriainen et al. (2017) Sci Rep. 7:40354).

In some embodiments, for example, bacterial infection may be caused by at least one bacterium selected from *Chlamydia, Bacilli, Bordetella*, botulism, *Campylobacter, Burkholderia*, anthrax, cholera, *Clostridium, Listeria, Conococcus, Corynebacterium*, diptheria, *Treponema, Brucella, Enterococcus, Mycoplasma, Borrelia, Erwinia, Escherichia, Francisella, Haemophilus, Heliobacter, Klebsiella, Xanthomonas Legionella*, Leptospira, leptospirosis, Lyme's disease, meningococcus, *Pneumococcus, Mycobacterium, Neisseria, Vibrio, Pasteurella, Pelobacter, Serratia*, plague, *Streptococcus, Proteus, Enterobacter, Pseudomonas, Rickettsia, Salmonella, Shigella, Staphylococcus* tetanus, and *Yersinia*.

In other embodiments, for example, viral infection may be caused by at least one virus selected from arboviral encephalitis virus, adenovirus, herpes simplex type I, herpes simplex type 2, Varicella-zoster virus, Epstein-barr virus, cytomegalovirus, herpesvirus type 8, papillomavirus, BK virus, coronavirus, echovirus, JC virus, smallpox, Hepatitis B, bocavirus, parvovirus B19, astrovirus, Norwalk virus, coxsackievirus, Hepatitis A, poliovirus, rhinovirus, severe acute respiratory syndrome virus, Hepatitis C, yellow fever, dengue virus, West Nile virus, rubella, Hepatitis E, human immunodeficiency virus (HIV), human T-cell lymphotropic virus (HTLV), influenza, guanarito virus, Junin virus, Lassa virus, Machupo virus, Sabia virus, Crimean-Congo hemorrhagic fever virus, ebola virus, Marburg virus, measles virus, molluscum virus, mumps virus, parainfluenza, respiratory syncytial virus, human metapneumovirus, Hendra virus, Nipah virus, rabies, Hepatitis D, rotavirus, orbivirus, coltivirus, vaccinia virus, and Banna virus.

In other embodiments, for example, fungal infection may be selected from thrush, *Coccidioides immitis, Blastomyces dermatitidis*, otomycosis, *Candida (albicans, krusei, glabrata, tropicalis*, etc.), *Tinea capitis, Tinea barbae, Tinea corporis, Tinea cruris, Tinea nigra, Sporothrix schenkii*, zygomycosis, chromoblastomycosis, *Cryptococcus (neoformans*, etc.), *Histoplasma capsulatum*, Tinea pedis, *Paracoccidioides brasiliensis*, phaeohyphomycosis, *Tinea favosa*, Mucorales *(mucor, absidia,* rhizophus), sporotrichosis, *Aspergillus (fumigatus, niger*, etc.), lobomycosis, mycetoma, onychomycosis, *piedra Pityriasis versicolor*, and rhinosporidiosis.

In some embodiments, for example, parasitic infection may be caused by at least one parasite selected from *Ascaris lumbricoides, Balantidium coli, Entamoeba hystolytica, Giardia lamblia, Naegleria fowleri, Necator americanus, Nippostrongylus brasiliensis, Strongyloides stercoralis, Cryptosporidium muris, Trypanosomatida gambiense, Trypanosomatida rhodesiense, Babesia microti, Trypanosoma cruzi, Leishmania mexicana, Leishmania braziliensis, Leishmania tropica, Leishmania donovani, Wuchereria bancrofti, Dracunculus medinensis, Toxoplasma gondii, Fasciola gigantica, Heterophyes heterophyes, Plasmodium vivax, Trypanosoma brucei, Plasmodium ovale, Plasmodium malariae, Plasmodium falciparum, Pneumocystis carinii, Trichomonas vaginalis, Histomonas meleagridis, Secementea, Trichuris trichiura, Acanthamoeba, Enterobius vermicularis, Ancylostoma duodenale*, blood flukes, liver flukes, intestinal flukes, lung flukes, *Schistosoma mansoni, Schistosoma haematobium, Schistosoma japonicum, Fasciola hepatica*, and *Paragonimus westermani*.

In certain embodiments, the present invention provides methods for treating cancer, wherein the cancer is selected from lung cancer, breast cancer, colon cancer, renal cancer, bladder cancer, thyroid cancer, prostate cancer, osteosarcoma and Hodgkin's lymphoma.

In certain embodiments, the present invention provides methods of modulating an immune response in a subject, comprising exposing a biological sample of the subject overexpressing T cell immunoreceptor with Ig and ITIM domains (TIGIT) and at least one of PD-L1 or PD-L2, to compound of formula (I) or a stereoisomer thereof or a pharmaceutically acceptable salt.

In certain embodiments, the present invention provides methods of modulating an immune response in a subject, comprising a) determining whether a biological sample from a subject overexpresses TIGIT; and b) if the sample overexpresses TIGIT, contacting the subject with a compound of formula (I) or a stereoisomer thereof or a pharmaceutically acceptable salt.

In certain embodiments, the present invention provides methods of modulating an immune response in a subject, further comprising:
  a) determining whether the sample overexpresses PD-L1 or PD-L2; and
  b) if the sample overexpresses TIGIT and either PD-L1 or PD-L2, contacting the subject with the compound of formula (I) or a stereoisomer thereof or a pharmaceutically acceptable salt.

In certain embodiments, the biological sample is selected from whole blood, plasma, serum, cells (e.g., tumor cells), saliva, urine, stool and tissue.

In certain embodiments, subject has a cancer, and, optionally, the sample comprises one or more cells from the cancer.

In certain embodiments, the subject has an infectious disease selected from a bacterial infection, a viral infection, a fungal infection, and a parasitic infection.

In certain embodiments, the control sample is obtained before the subject has received a compound of Formula (I) and the subject sample is obtained after the subject has received a compound of Formula (I).

The compounds of the present invention may be used as single drugs (monotherapy) or conjointly with one or more other agents (conjoint therapy). The compounds may be used by themselves or, preferably, in a pharmaceutical composition in which the compound is mixed with one or more pharmaceutically acceptable materials.

In certain embodiments, the prevention invention provides compounds for use in modulating an immune response mediated by both TIGIT signalling pathway and PD-1 signalling pathway in a subject.

In certain embodiments, immune response is modulated to treat diseases or disorders mediated by both TIGIT signalling pathway and PD-1 signalling pathway.

In certain embodiments, the cancer, according to this present disclosure, is selected from blastoma, breast cancer, epithelial cancer, colon cancer, lung cancer, melanoma, prostate cancer, renal cancer, bone cancer, pancreatic cancer, skin cancer, cancer of the head or neck, uterine cancer, ovarian cancer, colorectal cancer, rectal cancer, cancer of the anal region, cancer of the peritoneum, stomach cancer, testicular cancer, carcinoma of the fallopian tubes, carcinoma of the endometrium, cervical cancer, vaginal cancer, vulval cancer, cancer of the esophagus, cancer of the small intestine, cancer of the endocrine system, cancer of the thyroid gland, cancer of the parathyroid gland, cancer of the adrenal gland, sarcoma, cancer of the urethra, cancer of the penis, chronic or acute leukemia, solid tumors of childhood, Hodgkin's lymphoma, non-Hodgkin's lymphoma, cutaneous T cell lymphoma, mesothelioma, thymic carcinoma, myeloma, cancer of the bladder, cancer of the ureter, carcinoma of the renal pelvis, liver cancer, pancreatic cancer, post-transplant lymphoproliferative disorder (PTLD), neoplasm of the central nervous system (CNS), tumor angiogenesis, spinal axis tumor, brain stem glioma, pituitary adenoma, epidermoid cancer, salivary gland carcinoma, squamous cell cancer, abnormal vascular proliferation associated with phakomatoses, edema (such as that associated with brain tumors), Meigs' syndrome, Merkel cell carcinoma, and environmentally induced cancers.

In certain embodiments, the present invention provides a compound of formula (I) or a stereoisomer thereof or a pharmaceutically acceptable salt thereof, for use in modulating T cell immunoreceptor with Ig and ITIM domains (TIGIT) signaling pathway and programmed cell death 1 (PD-1) signaling pathway in a subject;

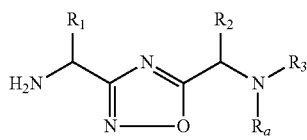

(I)

wherein,
R$_1$ represents hydrogen, —(C$_1$-C$_6$)alkyl optionally substituted with —OH, —COOH, aryl, heteroaryl, or aryl-OH;

R$_2$ represents hydrogen, —(C$_1$-C$_6$)alkyl optionally substituted with —OH, —SH, C(O)NH$_2$, —COOH, aryl, heteroaryl, or aryl-OH;

R$_a$ represents hydrogen; or R$_a$ and R$_2$ taken together with the atom to which they are attached form a pyrrolidine ring;

R$_3$ represents hydrogen or a group represented by formula (I'),

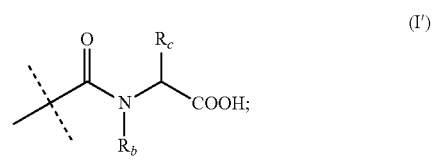

(I')

--- represents point of attachment;

R$_b$ represents hydrogen; or R$_b$ and R$_c$ taken together with the atoms to which they are attached form a pyrrolidine ring;

R$_c$ represents hydrogen, —(C$_1$-C$_6$)alkyl optionally substituted with —OH, —C(O)NH$_2$, COOH, aryl, or aryl-OH.

In certain embodiments, the present invention provides compound of formula

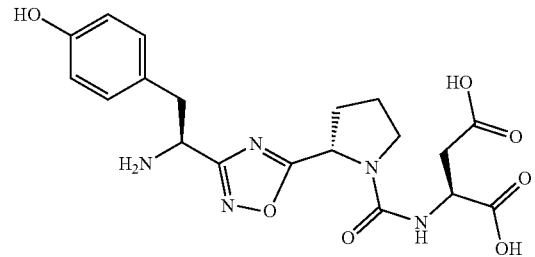 [SMILES: N[C@@H](Cc1ccc(O)cc1)c1noc([C@@H]2CCCN2C(=O)N[C@@H](CC(=O)O)C(=O)O)n1]

(compound 1) or a stereoisomer thereof or a pharmaceutically acceptable salt thereof, for use in modulating T cell immunoreceptor with Ig and ITIM domains (TIGIT) signaling pathway and programmed cell death 1 (PD-1) signaling pathway in a subject.

In certain embodiments, the present invention provides a compound of formula

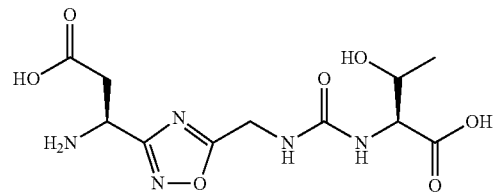 [SMILES: CC(O)[C@H](NC(=O)NCc1nc([C@@H](N)CC(=O)O)no1)C(=O)O]

(compound 2) or a stereoisomer thereof or a pharmaceutically acceptable salt thereof, for use in modulating T cell immunoreceptor with Ig and ITIM domains (TIGIT) signaling pathway and programmed cell death 1 (PD-1) signaling pathway in a subject.

In certain embodiments, the present invention provides a compound of formula

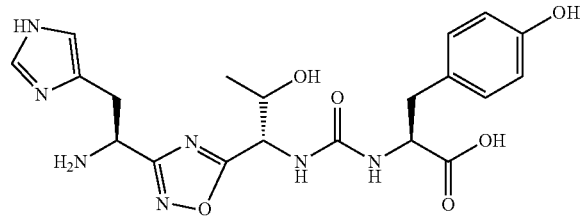 [SMILES: CC(O)[C@H](NC(=O)N[C@@H](Cc1ccc(O)cc1)C(=O)O)c1nc([C@@H](N)Cc2c[nH]cn2)no1]

(compound 3) or a stereoisomer thereof or a pharmaceutically acceptable salt thereof, for use in modulating T cell immunoreceptor with Ig and ITIM domains (TIGIT) signaling pathway and programmed cell death 1 (PD-1) signaling pathway in a subject.

In certain embodiments, the present invention provides a compound of formula

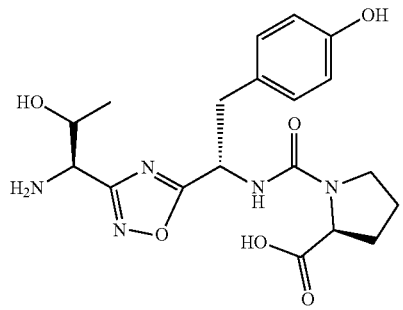 [SMILES: CC(O)[C@H](N)c1noc([C@H](Cc2ccc(O)cc2)NC(=O)N2CCC[C@H]2C(=O)O)n1]

(compound 19) or a stereoisomer thereof or a pharmaceutically acceptable salt thereof, for use in modulating T cell immunoreceptor with Ig and ITIM domains (TIGIT) signaling pathway and programmed cell death 1 (PD-1) signaling pathway in a subject.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody.

The term "control" refers to any reference standard suitable to provide a comparison to the expression products in the test sample. In certain embodiments, the control comprises obtaining a "control sample" from which expression product levels are detected and compared to the expression product levels from the test sample. Such a control sample may comprise any suitable sample, including but not limited to a sample from a control subject (can be stored sample or previous sample measurement) with a known outcome; normal tissue or cells isolated from a subject, cultured primary cells/tissues isolated from a subject, adjacent normal cells/tissues obtained from the same organ or body location of the subject, a tissue or cell sample isolated from a normal subject, or a primary cells/tissues obtained from a depository. In certain embodiments, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome or receiving a certain treatment. It will be understood by those of skill in the art that such control samples and reference standard expression product levels can be used in combination as controls in the methods of the present invention.

The "normal" level of expression of TIGIT is the level of expression of TIGIT in cells of a subject, e.g., a human patient, not in need of immune response modulation. An "over-expression" or "significantly higher level of expression" of a biomarker refers to an expression level in a test sample that is greater than the standard error of the assay employed to assess expression, and is preferably at least about 10%, and more preferably about 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of TIGIT in a control sample (e.g., sample from a healthy subject not in need of immune modulation, or from a healthy tissue sample obtained from the same subject) and preferably, the average expression level of the biomarker in several control samples. A "significantly lower level of expression" of a biomarker refers to an expression level in a test sample that is at least about 10%, and more preferably about 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not in need of immune modulation) and preferably, the average expression level of the biomarker in several control samples.

The term "sample" used for detecting or determining the presence or level of the TIGIT gene is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In some embodiments, the disclosed methods further comprise obtaining the sample from the subject prior to detecting or determining the presence or level of the TIGIT gene.

The pharmaceutical composition may be administered by oral or inhalation routes or by parenteral administration route. For example, compositions can be administered orally, by intravenous infusion, topically, intraperitoneally, intravesically or intrathecally. Examples of parenteral administration includes but not limited to intraarticular (in the joints), intravenous, intramuscular, intradermal, intraperitoneal and subcutaneous routes. Suitable liquid compositions may be aqueous or non-aqueous, isotonic sterile injection solutions and may contain antioxidants, buffers, bacteriostats and solutes that render the formulation isotonic with the blood of the intended recipient and aqueous and non-aqueous sterile suspensions that can include suspending agents, solubilizers, thickening agents, stabilizers and preservatives. Oral administration, parenteral administration, subcutaneous administration and intravenous administration are preferred methods of administration.

The dosage of the compounds of the present invention varies depending on a patient's age, weight or symptoms, as well as the compound's potency or therapeutic efficacy, the dosing regimen and/or treatment time. Generally, suitable routes of administration may, for example, include oral, eyedrop, rectal, transmucosal, topical or intestinal administration; parenteral delivery, including intramuscular, subcutaneous, intramedullary injections, as well as intrathecal, direct intraventricular, intravenous, intraperitoneal, intranasal or intraocular injections. The compounds of the invention may be administered in an amount of 0.5 mg or 1 mg up to 500 mg, 1 g or 2 g per dosage regimen. The dosage may be administered once per week, once per three days, once per two days, once per day, twice per day, three times per day or more often. In alternative embodiments, in certain adults the compound can be continuously administered by intravenous administration for a period of time designated by a physician. Since the dosage is affected by various conditions, an amount less than or greater than the dosage ranges contemplated about may be implemented in certain cases. A physician can readily determine the appropriate dosage for a patient undergoing therapeutic treatment.

Combination Therapy

The compounds of the present disclosure may be administered in combination with one or more other drugs (1) to complement and/or enhance effect of the compound of Formula (I), (2) to modulate pharmacodynamics, improve absorption, or reduce dosage of the compound of Formula (I), and/or (3) to reduce or ameliorate the side effects of the compound Formula (I). As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds. The respective compounds may be administered by the same or different route and the same or different method. In some embodiments, the combined effect of conjoint therapy is detectable through immune effects.

The dosage of the other drug can be a dosage that has been clinically used, or may be an altered dosage such that the dosage is effective when administered in combination with a compound of the present disclosure. The ratio of the compound of the present disclosure and the other drug can vary according to age and weight of a subject to be administered, administration method, administration time, disorder to be treated, symptom and combination thereof. For example, the other drug may be used in an amount of 0.01 to 100 parts by mass, based on 1 part by mass of the compound of the present disclosure.

Conjoint therapy can be employed to treat any diseases discussed herein. In certain embodiments, a compound of Formula (I) of the disclosure may be conjointly administered with another therapeutic agent, e.g., an anti-cancer agent, an anti-viral agent, a cytokine or an immune agonist. In some embodiments, the other therapeutic agent is selected from CTLA-4 antagonists, PD-1 antagonists, PD-L1 antagonists, or PD-L2 antagonists, and EGFR antagonists.

TIGIT antagonizing agents are expected to rescue NK cell function from the TIGIT-mediated suppression. Since NK cells contribute to the efficacy of many of the antibodies targeting cancer cell surface proteins (such as HER2, EGFR, CD38 and CD20 antibodies) through antibody-mediated cellular cytotoxicity (ADCC), TIGIT agents are expected to work synergistically in combination with many of the anti-cancer antibodies such as anti-HER2 antibodies, anti-EGFR antibodies, anti-CD38 antibodies and anti-CD20 antibodies.

Agents for Combination Therapies

In certain embodiments, a compound of Formula (I) can be conjointly administered with another therapeutic agent, e.g., 1) an aldosterone synthase inhibitor;
2) an ALK inhibitor; an apoptosis inducer;
3) an aromatase inhibitor;
4) a CART cell (e.g., a CART cell targeting CD19);
5) a BCR-ABL inhibitor;
6) a BRAF inhibitor;
7) a CDK4/6-inhibitor;
8) a CEACAM (e.g., CEACAM-1, -3 and/or -5) inhibitor;
9) a c-KIT inhibitor;
10) a c-MET inhibitor;
10) a cRAP inhibitor;
11) a CTLA4 inhibitor;
12) a cytochrome P450 inhibitor (e.g., a CYP17 inhibitor);
13) an EGF inhibitor;
14) an ERK1/2 ATP inhibitor;
15) an FGF inhibitor (e.g., a FGFR2 or FGFR4 inhibitor);
16) a Flt3 inhibitor (e.g., FLK2/STK1);
17) a P-Glycoprotein 1 inhibitor;
18) a HDAC inhibitor;
19) a HDM2 inhibitor;
20) a HER3 inhibitor;
21) a histamine release inhibitor;
22) an HSP90 inhibitor:
23) an IAP inhibitor;
24) an IDH inhibitor;
25) an IDO inhibitor
26) an IGF-1R inhibitor;
27) an iron chelating agent;
28) a Janus inhibitor;
29) a LAG-3 inhibitor;
30) an M-CSF inhibitor;
31) a MEK inhibitor;
32) an mTOR inhibitor;
33) a p53 inhibitor (e.g., an inhibitor of a p53/Mdm2 interaction);
34) a PDGFRβ inhibitor;
35) a PKC inhibitor;
36) a PI3K inhibitor;
37) a PIM inhibitor;
38) a PRLR inhibitor;
39) a Raf kinase C inhibitor;
40) a smoothened (SMO) receptor inhibitor;
41) a somatostatin agonist and/or a growth hormone release inhibitor;
42) a transduction modulator and/or angiogenesis inhibitor;
43) a VEGFR-2 inhibitor (e.g., FLK-1/KDR);
44) a tyrosine kinase inhibitor (e.g., CSF-1R tyrosine kinase);
45) a Wnt signaling inhibitor 46) a Bcl-2 inhibitor;
47) a Mcl-1 inhibitor;
48) a BTK inhibitor;
49) dual active molecules such as CUDC-907 (a dual PI3K/HDAC inhibitor); and
50) BET bromodomain inhibitor.

Additional therapeutic agents suitable for conjoint administration with the compounds and compositions disclosed herein have been described, for example, in the following publications: WO2016/100882; WO2016/054555; WO2016/040892; WO2015/097536; WO2015/088847; WO2015/069770; WO2015/026634; WO 2015/009856; EP 1377609 B1; Antonia, et al. Clin. Cancer Res. 2014 20:6258-6268; and Melero, et al. Nature Reviews Cancer 2015 15:457-472. Each publication is incorporated herein by reference in its entirety.

For example, in the methods of the disclosure directed to the treatment of cancer, the compound of the present disclosure can be used with another chemotherapeutic conjointly as a single pharmaceutical composition or a combination of different pharmaceutical compositions. Non-limiting examples of the chemotherapeutic agent include an alkylation agent, nitrosourea agent, antimetabolites, anticancer antibiotics, vegetable-origin alkaloids, topoisomerase inhibitors, hormone drugs, hormone antagonists, leucopenia (neutropenia) treatment drugs, thrombocytopenia treatment drugs, antiemetics, aromatase inhibitors, P-glycoprotein inhibitors, platinum complex derivatives, other immunotherapeutic drugs and other anticancer drugs.

Exemplary cytotoxic agents that can be administered conjointly include antimicrotubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors, and radiation (e.g., local or whole body irradiation).

Non-limiting examples of additional therapeutic agents include, but are not limited to, peptides, polypeptides, proteins, fusion proteins, nucleic acid molecules, small molecules, mimetic agents, synthetic drugs, inorganic molecules, and organic molecules.

The conjoint therapy can include, other compatible agents, e.g., a chemotherapeutic agent, a cytokine therapy, an interferon therapy (e.g., interferon-α, β, or γ; interferon α-2a; interferon α-2b; interferon α-m; interferon α-n3; interferon β-Ia; and interferon γ-Ib), an interleukin therapy (e.g., IL-1, IL-2, IL-2Rβ, IL-2Rγ, IL-3, IL-7, IL7Rα, IL-11, IL-12, IL-15, and IL-21), a cluster of differentiation (CD) protein (e.g., CD2, CD4, CD7, CD8a, CD80, CD11a/CD18, CD11b, CD11c, CD11d, CD18, CD19, CD19a, CD20, CD27, CD28, CD29, CD30, CD40, CD40L, CD49a, CD49D, CD49f, CD69, CD84, CD96, CD100, CD103, CD137, CD160, CD226, CD229, CD278) a co-stimulatory modulator, e.g., an agonist (e.g., an agonistic antibody or antigen-binding fragment thereof, or soluble fusion) of an MHC class I molecule, a TNF receptor protein, an immunoglobulin-like protein, a Toll ligand receptor, a CD83 ligand, a cytokine receptor, an integrin, signaling lymphocytic activation molecules (SLAM proteins), an activating NK cell receptor, an antibody therapy, a viral therapy, gene therapy or a combination thereof.

Chemotherapeutic and other therapeutic agents that may be conjointly administered with compounds of the disclosure include, but are not limited to: abiraterone, abraxane, aceglatone, acivicin, aclacinomysin, actimid, actinomycin, aflibercept, aldesleukin, aldophosphamide glycoside alectinib, alendronate, alitretinoin, altretamine, aminoglutethimide, aminolevulinic acid, aminopterin, amsacrine, anastrozole, ancitabine, angiostatin, angiozyme, anguidine, ansamitocin, anthramycin, antithrombin III, apatinib, arabinoside, arboplatin, asparaginase, authramycin, axitinib, azacitidine, azaserine, azetepa, azotomycin, 6-azauridine, baricitinib, batimastat, bendamustine, benimetinib, benzodopa, bestrabucil, bexarotene, bicalutamide, bisantrene, bleomycin, bortezomib, bosutinib, brequinar, brivanib, bryostatin, bropirimine, bullatacin, bullatacinone, buserelin, busulfan, cactinomycin, calicheamicin, callystatin, calusterone, caminomycin, campothecin, capecitabine, carabicin, carboplatin, carboquone, carfilzomib, carmofur, carmustine, carubicin, carzelesin, carzinophilin, cedefingol, cediranib, chlomaphazine, chlorambucil, chloroquine, chlorozotocin, cholophosphamide, chromomycin, cirolemycin, cisplatin, cisdichlorodiamine platinum (II), cisplatin, cladribine, clodronate, cobimetinib, colchicine, crisnatol, crizotinib, cryptophycin 1, cryptophycin 8, cyclophosphamide, cyproterone, cytarabine, cytochalasin B, cytosine arabinoside, dabrafenib, dacarbazine, dactinomycin, danoprevir, dasatinib, diaziquone, dibromomannitol, daunorubicin, decitabine, defofamine, degarelix, 1-dehydrotestosterone, delanzomib, demecolcine, demethoxyviridin, denileukin, denenicokin, denopterin, desacetylravidomycin, detorubicin, dexamethasone, dexormaplatin, dezaguanine, diaziquone, 6-diazo-5-oxo-L-norleucine, dichloroacetate, dideoxyuridine, dienestrol, diethylstilbestrol, diftitox, difluoromethylomithine, dihydroxyanthracindione, dinaciclib, docetaxel, dolastatin, dovitinib, doxifluridine, doxorubicin, doxycycline, droloxifene, dromostanolone, duazomycin, duocarmycin, dynemicin, edatrexate, eflomithine, elliptinium acetate, eleutherobin, emetine, emsirolimus, encorafenib, enloplatin, enocitabine, enpromate, epipropidine, epirubicin, epithilone, epitiostanol, erbulozole, erismodegib, erlotinib, esorubicin, esperamicin, estradiol, estramustine, etanidazole, ethidium bromide, 2-ethylhydrazide, etidronate, etoglucid, etoposide, everolimus, exemestane, fadrozole, fazarabine, fenretinide, filgrastim, floxuridine, fludarabine, fludrocortisone, fluorouracil, fluoxymesterone, flurocitabine, flutamide, foretinib, formestane, fosquidone, fotemustine, frolinic acid, gacytosine, gallium nitrate, galunisertib, gandotinib, gefitinib, geldanamycin, gemcitabine, genistein, glucocorticoids, goserelin, gramicidin D, herbimycin, hiltonol, 4-hydroxytamoxifen, hydroxyurea, ibandronate, idarubicin, ifosfamide, ilmofosine, imatinib, imiquimod, improsulfan, indoximod, interferon, iproplatin, irinotecan, ironotecan, ixazomib, keoxifene, laherparepvec, lameotide, lapatinib, lenalidomide, lestaurtinib, letrozole, leucovorin, leuprolide, lentinan, levamisole, liarozole, lidocaine, linifanib, lometrexo, lomustine, lonidamine, losoxantrone, marcellomycin, marizomib, masitinib, masoprocol, maytansyne, maytansinol, mechlorethamine, mechlorethamine oxide hydrochloride, mannomustine, medroxyprogesterone, megestrol, melengestrol, menogaril, melphalan, mepitiostane, mercaptopurine, mesna, metformin, methotrexate, metoprine, meturedopa, mithramycin, mitobronitol, mitoguazone, mitolactol, mitomycin, mitosper, mitotane, mitoxantrone, momelotinib, montanide, mopidamol, motesanib, motolimod, mycophenolic acid, mylotarg, nab-paclitaxel, navelbine, neratinib, nilotinib, nilutamide, nimustine, nitracrine, nocodazole, nogalamycin, novantrone, novembichin, obinutuzumab, octreotide, olivomycin, onapristone, ormaplatin, oxaliplatin, paclitaxel, pacritinib, palbociclib, pamidronate, pancratistatin, panobinostat, pazopanib, pegaptanib, pegaspargase, pegfilgrastim, peginterferon α-2b, pelitinib, pemetrexed, pentostatin, N4-pentoxycarbonyl-5-deoxy-5-fluorocytidine, peplomycin, perifosine, phenamet, phenesterine, pimasertib, pipobroman, piposulfan, pirarubicin, plicamycin, podophyllinic acid, polifeprosan, pomalidomide, porfimer, porfromycin, potfiromycin, prednimustine, procaine, procarbazine, propranolol, pteropterin, puromycin, quelamycin, raltitrexed, raloxifene, ranimustine, rapamycin, ravidomycin, razoxane, regorafenib, risedronate, resiquimod, rituximab, rodorubicin, rogletimide, roridin, ruxolitinib, safingol, sarcodictyin, selumetinib, semaxanib, semustine, simapimod, simtrazene, sirolimus, sizofiran, sorafenib, sparfosate, sparsomycin, spirogermanium, spiromustine, spiroplatin, spongistatin, streptonigrin, streptozocin, sulofenur, sunitinib, suramin, talisomycin, tamoxifen, talimogene, tasocitinib, taxol, tegafur, telatinib, teloxantrone, temoporfin, temozolomide, temsirolimus, teniposide, tenuazonic acid, teroxirone, testolactone, testosterone, tetracaine, tezacitibine, thalidomide, thiamiprine, thioguanine, thiotepa, tiazofurin, tiludronate, tirapazamine, titanocene, tivozanib, toceranib, tofacitinib, topoisomerase inhibitor RFS 2000, topotecan, toremifene, tozasertib, trametinib, trastuzumab, triaziquone, tretinoin, 2, 2',2"-trichlorotriethylamine, triethylenemelamine, triethylenephosphoramide, triethylenethiophosphaoramide, trilostane, trimethylolomelamine, trimetrexate, triptorelin, trofosfamide, tubercidin, tuvizanib, uracil mustard, ubenimex, uredopa, urethane, vandetanib, vapreotide, vargatef, vatalanib, vemurafenib, verracurin, verteporfin, vinblastine, vincristine, vindesine, vinepidine, vinglycinate, vinleurosine, vinorelbine, vinrosidine, vinzolidine, vorozole, vismodegib, xeloda, zactima, zeniplatin, zinostatin, Ziv-aflibercept, zoledronate, and zorubicin.

In certain embodiments, exemplary chemotherapeutic agents include, but are not limited to, cytokines such as ABT-869, ACP-196, ADXS11-001, ADXS31-142, AEE788, AG-490, AM0010, AMN-107, AMP-224, AMP-514, AP24534, ARRY-142886, AST-6, AZD1480, AZD4547, AZD6094, AZD6244, AZD8055, AZD9291, B7-H3, BAFFR, 4-1BB, BEZ235, BGT 226, BHG712, BIBF 1120, BIBW2992, BIX 02188, BJG398, BKM-120, BMS-599626, BMS-690154, BMS-777607, BMS-911543, BMS-936558, BMS-936559, BMS-986016, BRAF V600E, BTLA, BUW078, BYL719, CAL-101, CAL-263, CBI-TMI, CC-1065, CC-4047, CC-5013, CDS, CDX-1127, CEACAM1, CEP-701, CEP-11981, CGM097, Chi Lob 7/4, CI-1040, CO-1686, CP-673451, CP-870,893, CpG 7909, CPT-11, CRTAM, CT-011, CTL019, CTLA-4, CUDC-101, CYC116, CYT 387, DCC-2036, DNAM1, E6201, E7080, EGF816, FOLFOX6, G02443714, G-38963, GADS, GC1008, G-CSF, GDC-0032, GDC-0973, GDC-0980, GITR, GM CSF, GR-MD-02, GSK1059615, GVAX, HVEM (LIGHTR), IA4, ICAM-1, ICOS, IMC-TR1, IMP321, INC280, INC424, INCB18424, INCB024360, INCB028050, IPH2012, IPI926, IRX-2, ISA 51VG, ITGA4, ITGA6, ITGAD, ITGAE, ITGAL, ITGAM, ITGAX, ITGB1, ITGB2, ITGB7, JNJ-26483327, Ki8751, KIRDS2, KU-0063794, KW-289LAT, LBH589, LCL161, LGH447, LTBR, LDK378, LEE011, LGX818, LIGHT, LJM716, LY117018, LY2157299, LY294002, LY2940680, M-CSF, MARTI, MDX-1105, MDX-1106, MEDI0562, MEDI4736, MEDI4737, MEDI6383, MEDI6469, MEK162, MG-132, MGCD265, MK-3475, MK 4166, MM-121, MOXR0916, MP470, MPDL3280A, MSB-0010718C, NKG2C, NKG2D, NKp30, NKp44, NKp46, NKp80 (KLRF1), NY-ESO-1, ODC-0879, ODC-0980, ONX-0912, ODC-0941, OSI-027, OSI-930, OSK-1120212, OSK 2118436, OSK 2126458, OX40, P529, PAG/Cbp, PD153035, PD173074, PD0325901, PF-299804, PF-02341066, PF-04217903, PF-046915032, PF-05082566, PD98059, Poly(I:C), PKI-587, PLX4032, PLX4720, PSGL1, PSK, PX-886, Rad-001, RAF265, rHIgM12B7, R07204, R04987655, R06895882, R07009789, SAR 245408, SAR 245409, SB-1317, SB-1518, SB-1578, SELPLG, SF1126, SGX523, SLAM, SLAMF4, SLAMF6, SLAMF7, SLAML_BLAME, SLP-76, SU 5402, T2 toxin, TEW 7197, TGN1412, TNFR2, TRANCE/RANKL, TriMix-DC, TRP-2, TRX518, TSU-68, VLA1, VLA-6, WYE-354, WZ3146, WZ4002, WZ8040, XL-147, XL-184, XL-228, XL-281, XL-647, XL-756, XL-765, XL-880, Yttrium90/MX-DTPA, and YW243.55.S70.

Exemplary paclitaxel agents that can be used conjointly with compounds disclosed herein include, but are not limited to, nanoparticle albumin-bound paclitaxel (ABRAXANE, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG 105 (Angiopep-2 bound to three molecules of paclitaxel, marketed by ImmunoGen), paclitaxel-EC-1 (paclitaxel bound to the erbB2-recognizing peptide EC-1; see Li et al., Biopolymers (2007) 87:225-230), and glucose-conjugated paclitaxel (e.g., 2'paclitaxel methyl 2-glucopyranosyl succinate, see Liu et al., Bioorganic & Medicinal Chemistry Letters (2007) 17:617-620).

In certain embodiments, exemplary chemotherapeutic agents include, but are not limited to:
1) (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide;
2) ((1R,9S,12S,15R,16E,18R,19R,21R, 23S, 24E, 26E, 28E, 30S, 32S, 35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29,35-hexamethyl-11,36-dioxa-4-azatricyclo[30.3.1.04,9]hexatriaconta-16,24,26,28-tetraene-2,3,10,14,20-pentaone);
3) (S)-1-(4-chlorophenyl)-7-isopropoxy-6-methoxy-2-(4-{methyl-[4-(4-methyl-3-oxopiperazin-1-yl)-trans-cyclohexylmethyl]-amino}phenyl)-1,4-dihydro-2H-isoquinolin-3one;
4) N-(4-((1R,3S,5S)-3-amino-5-methylcyclohexyl)pyridin-3-yl)-6-(2,6-difluoro phenyl)-5-fluoropicolinamide;
5) anti-HER3 monoclonal antibody or antigen binding fragment thereof, that comprises a VH of SEQ ID NO: 141 and VL of SEQ ID NO: 140, as described in U.S. Pat. No. 8,735,551;
6) (E)-N-hydroxy-3-(4-(((2-(2-methyl-1H-indol-3-yl)ethyl) amino)methyl)phenyl) acrylamide;
7) (3R)-3-cyclopentyl-3-[4-(7H-pyrrolo-[2,3-d]pyrimidin-4-yl)-1H-pyrazol-1-yl]propanenitrile; and/or
8) 8-(2,6-difluoro-3,5-dimethoxy-phenyl)-quinoxaline-5-carboxylic acid (4-dimethylaminomethyl-1H-imidazol-2-yl)-amide.

In other embodiments, exemplary chemotherapeutic agents include, but are not limited to,
1) 3-(1H-indol-3-yl)-4-[2-(4-methyl-1-piperazinyl)-4-quinazolinyl]-1H-pyrrole-2,5-diane;
2) 5-(2,4-dihydroxy-5-isopropylphenyl)-N-ethyl-4-(4-(morpholinomethyl) phenyl)isoxazole-3-carboxamide;
3) 2-methyl-2-(4-(3-methyl-2-oxo-8-(quinolin-3-yl)-2,3-dihydro-1H-imidazo[4,5-c]quinolin-1-yl)phenyl)propanenitrile (dactolisib);
4) Compound D (CYP17 inhibitor);
5) 4-[3,5-bis(2-hydroxyphenyl)-1H-1,2,4-triazol-1-yl]-benzoic acid (defeasirox);

6) 4,4'-(1H-1,2,4-triazol-1-ylmethylene)bis-benzonitrile (letrozole);
7) (4S,5R)-3-(2'-amino-2-morpholino-4'-(trifluoromethyl)-[4,5'-bipyrimidin]-6-yl)-4-(hydroxymethyl)-5-methyl-oxazolidin-2-one;
8) (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one;
9) 4-[(4-methyl-1-piperazinyl)methyl]-N-[4-methyl-3-[[4-(3-pyridinyl)-2-pyrimidinyl]amino]phenyl]-methane-sulfonate-benzamide;
10) 4-[(R)-6,7-dihydro-5H-pyrrolo[1,2-c]imidazol-5-yl]-3-fluorobenzonitrile (osilodrostat);
11) N-[6-[(2R,6S)-2,6-dimethyl-4-morpholinyl]-3-pyridinyl]-2-methyl-4'(tri fluoromethoxy)-[1,1'-biphenyl]-3-carboxamide, diphosphate (sonidegib phosphate);
12) (R)-2-(5-(4-(6-benzyl-4,5-dimethylpyridazin-3-yl)-2-methylpiperazin-1-yl) pyrazin-2-yl)propan-2-ol;
13) Compound M (human monoclonal antibody to PRLR);
14) 2-(2',3-dimethyl-[2,4'-bipyridin]-5-yl)-N-(5-(pyrazin-2-yl)pyridin-2-yl) acetamide;
15) 7-cyclopentyl-N,N-dimethyl-2-((5-((1R,6S)-9-methyl-4-oxo-3,9-diaza bicyclo[4.2.1]nonan-3-yl)pyridin-2-yl)amino)-7H-pyrrolo[2,3-d]pyrimidine-6-carboxamide;
16) Compound P (FGFR2 and/or FGFR4 antibody drug conjugate, mAb 12425);
17) Compound Q (monoclonal antibody of Fab to M-CSF);
18) N-[(9S,10R,11R,13R)-2,3,10,11,12,13-hexahydro-10-methoxy-9-methyl-1-oxo-9,13-epoxy-1H,9H-diindolo[1,2,3m]pyrrolo[3,4-j][1,7]benzodiazonin-11-yl]-N-methyl-benzamide (midostaurin);
19) 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine;
20) cyclo((4R)-4-(2-aminoethylcarbamoyloxy)-L-prolyl-L-phenylglycyl-D-tryptophyl-L-lysyl-4-O-benzyl-L-tyrosyl-L-phenylalanyl-) (pasireotide diaspartate);
21) 1-amino-5-fluoro-3-[6-(4-methyl-1-piperazinyl)-1H-benzimidazol-2-yl]-2(1H)-quinolinone (dovitinib);
22) 8-(6-methoxy-pyridin-3-yl)-3-methyl-1-(4-piperazin-1-yl-3-trifluoromethyl-phenyl)-1,3-dihydro-imidazo[4,5-c]quinolin-2-one;
23) N6-(2-isopropoxy-5-methyl-4-(1-methylpiperidin-4-yl)phenyl)-N4-(2-(isopropylsulfonyl)phenyl)-1H-pyrazolo[3,4-d]pyrimidine-4,6-diamine;
24) 3-(4-(4-((5-chloro-4-((5-methyl-1H-pyrazol-3-yl)amino)pyrimidin-2-yl)amino)-5-fluoro-2-methylphenyl)piperidin-1-yl)thietane 1, 1-dioxide;
25) 5-chloro-N2-(2-fluoro-5-methyl-4-(1-(tetrahydro-2H-pyran-4-yl)piperidin-4-yl)phenyl)-N4-(5-methyl-1H-pyrazol-3-yl)pyrimidine-2,4-diamine;
26) 5-chloro-N2-(4-(1-ethylpiperidin-4-yl)-2-fluoro-5-methylphenyl)-N4-(5-methyl-1H-pyrazol-3-yl)pyrimidine-2,4-diamine;
27) 6-[(2S,4R,6E)-4-methyl-2-(methylamino)-3-oxo-6-octenoic acid]cyclo sporine D. Amdray, PSC833, [3'-Desoxy-3'-oxo-MeBmt]1-[Val]2-cyclosporin (valspodar);
28) N-(4-chlorophenyl)-4-(4-pyridinylmethyl)-1-phthalazinamine succinate (vatalanib succinate);
29) Compound CC (IDH inhibitor);
30) (R)—N-(4-(chlorodifluoromethoxy)phenyl)-6-(3-hydroxypyrrolidin-1-yl)-5-(1H-pyrazol-5-yl)nicotinamide;
31) Compound EE (cRAF inhibitor);
32) Compound FF (ERK1/2 ATP competitive inhibitor); and
33) 4-((2-(((1R,2R)-2-hydroxycyclohexyl)amino)benzo[d]thiazol-6-yl)oxy)-N-methylpicolinamide. See, e.g., WO2016/100882, which is incorporated herein by reference in its entirety.

In certain embodiments, exemplary therapeutic agents for conjoint administration are monoclonal antibodies or fragments thereof (see e.g., Bolliger (1993) Proc. Natl. Acad. Sci. USA 90:6444-6448; Poljak (1994) Structure 2:1121-1123). These therapeutic monoclonal antibodies and/or fragments thereof include, but are not limited to, anti-LAG-3 monoclonal antibody, anti-PD-1 antibody, anti-PD-L1 antibody, anti-PD-L2 antibody, anti-TIM-3 antibody, anti-CTLA-4 antibody, anti-TIGIT antibody, anti-OX40 antibody, anti-GITR antibody, adalimumab, afatinib, afutuzumab, alemtuzumab, atezolizumab, avelumab, axitinib, basiliximab, bavituximab, belimumab, bevacizumab, brentuximab, canakinumab, certolizumab, cetuximab, daclizumab, denosumab, durvalamab, eculizumab, efalizumab, elotuzumab, fostamatinib, gemtuzumab ozogamicin, golimumab, ibritumomab tiuxetan, infliximab, ipilimumab, lambrolizumab, lapatinib, lenvatinib, lirilumab, mogamulizumab, motavizumab, mubritinib, natalizumab, nivolumab, obinutuzumab, ofatumumab, omalizumab, palivizumab, panitumumab, pegaptani, pembrolizumab, pertuzumab, pidilizumab, ranibizumab, raxibacumab, rilotumumab, rituximab, tocilizumab, tositumomab-I-13, trastuzumab, tremelimumab, urelumab, ustekinumab, and varlilumab.

Combination therapies can also include administration of bispecific antibodies. Bispecific antibodies can be used to target two separate antigens. For example anti-Fc receptor/anti-tumor antigen (e.g., Her-2/neu) bispecific antibodies have been used to target macrophages to sites of tumor. This targeting may more effectively activate tumor specific responses. The T cell arm of these responses would by augmented by the use of PD-1 blockade. Alternatively, antigen may be delivered directly to DCs by the use of bispecific antibodies which bind to tumor antigen and a dendritic cell specific cell surface marker.

Other antibodies which may be used to activate host immune responsiveness can be used in combination with the combination therapies described herein. These include molecules on the surface of dendritic cells which activate DC function and antigen presentation. Anti-CD40 antibodies are able to substitute effectively for T cell helper activity (Ridge, J. et al. (1998) Nature 393: 474-478) and can be used in conjunction with PD-1 antibodies (Ito, N. et al. (2000) Immunobiology 201 (5) 527-40). Antibodies to T cell costimulatory molecules such as CTLA-4 (e.g., U.S. Pat. No. 5,811,097), OX-40 (Weinberg, A. et al. (2000) Immunol 164: 2160-2169), 4-1BB (Melero, I. et al. (1997) Nature Medicine 3: 682-685 (1997), and ICOS (Hutloff, A. et al. (1999) Nature 397: 262-266) may also provide for increased levels of T cell activation.

Immunomodulatory agents and therapies that are suitable for use in the compositions and conjoint methods described herein include, but are not limited to, anti-T cell receptor antibodies such as anti-CD3 antibodies (e.g., Nuvion (Protein Design Labs), OKT3 (Johnson & Johnson), or anti-CD20 antibodies Rituxan (IDEC), antiCD52 antibodies (e.g., CAMPATH 1H (Ilex)), anti-CD11a antibodies (e.g., Xanelim (Genentech)); anti-cytokine or anti-cytokine receptor antibodies and antagonists such as anti-IL-2 receptor antibodies (Zenapax (Protein Design Labs)), anti-IL-6 receptor antibodies (e.g., MRA (Chugai)), and anti-IL-12 antibodies (CNT01275 (Janssen)), anti-TNFalpha antibodies (Remicade (Janssen)) or TNF receptor antagonist (Enbrel (Immunex)), anti-IL-6 antibodies (BE8 (Diaclone)) and siltuximab (CNT032 (Centocor)), and antibodies that immunospecifically bind to tumor-associated antigens (e.g., trastuzimab (Genentech)).

The combination therapies disclosed herein can be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) J. Immunol. 173:4919-28). Non-limiting examples of tumor vaccines that can be used include peptides of melanoma antigens, such as peptides of gp100, MAGE antigens, Trp-2, MART I and/or tyrosinase, or tumor cells transfected to express the cytokine GM-CSF.

Compounds disclosed herein can be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) Science 266: 2011-2013). (These somatic tissues may be protected from immune attack by various means). Tumor antigens may also be "neo-antigens" expressed in cancer cells because of somatic mutations that alter protein sequence or create fusion proteins between two unrelated sequences (ie. bcr-abl in the Philadelphia chromosome), or idiotype from B cell tumors.

Compounds disclosed herein can be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43). In some embodiments, vaccination with immunoglobulin idiotype produced by malignant plasma cells is used. Other therapeutic vaccines include, but are not limited to, sipuleucel-T, gp100 vaccine, HPV-16 vaccination, and GVAX pancreas vaccine.

Other tumor vaccines may include the proteins from viruses implicated in human cancers such a Human Papilloma Viruses (HPV), Hepatitis Viruses (HBV and HCV), Kaposi's Herpes Sarcoma Virus (KHSV) and Preferentially Expressed Antigen In Melanoma (PRAME). In certain embodiments, the vaccine is selected from a viral vector vaccine, bacterial vaccine, cell-based vaccine, DNA vaccine, RNA vaccine, peptide vaccine, or protein vaccine. See, e.g., Jeffrey Schlom, "Therapeutic Cancer Vaccines: Current Status and Moving Forward," J Natl Cancer Inst; 104:599-613 (2012). Another form of tumor specific antigen which may be used in conjunction with PD-1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) Science 269: 1585-1588; Tamura, Y. et al. (1997) Science 278:117-120).

Exemplary agents that can be conjointly administered with compounds disclosed herein include a therapeutic cancer vaccine or adoptive T cell therapy. In certain embodiments, the therapeutic cancer vaccine is a dendritic cell vaccine. The dendritic cell vaccine can be composed of autologous dendritic cells and/or allogeneic dendritic cells. In certain embodiments, the autologous or allogeneic dendritic cells are loaded with cancer antigens prior to administration to the subject. In certain embodiments, the autologous or allogeneic dendritic cells are loaded with cancer antigens through direct administration to the tumor. In certain embodiments, the adoptive T cell therapy comprises autologous and/or allogenic T-cells. In certain embodiments, the autologous and/or allogenic T-cells are targeted against tumor antigens.

In certain embodiments, non-limiting examples of cancer vaccines include tumor cell vaccines, antigen vaccines, dendritic cell vaccines, DNA vaccines, and vector based vaccines. Antigen vaccines boost the immune system by using one or more antigens, such as peptides. Antigen vaccines may be specific for a certain type of cancer because each tumor type may be identified by specific antigen profiles. Dendritic cell vaccines are often autologous vaccines, and must often be made individually for each subject. Non-limiting examples of dendritic vaccines are Sipuleucel-T and DCvax. For preparing DNA vaccines, vectors can be engineered to contain specific DNAs that can be injected into a subject which leads to the DNA being taken up by cells. Once the cells take up the DNA, the DNA will program the cells to make specific antigens, which can then provoke the desired immune response.

Pancreatic Cancer

Exemplary agents that that can be used conjointly with compounds disclosed herein for the treatment of pancreatic cancer include, but are not limited to, TAXOL, an albumin-stabilized nanoparticle paclitaxel formulation (e.g., ABRAXANE) or a liposomal paclitaxel formulation); gemcitabine (e.g., gemcitabine alone or in combination with AXP107-11); other chemotherapeutic agents such as oxaliplatin, 5-fluorouracil, capecitabine, rubitecan, epirubicin hydrochloride, NC-6004, cisplatin, docetaxel (e.g., TAXOTERE), mitomycin C, ifosfamide; interferon; tyrosine kinase inhibitor (e.g., EGFR inhibitor (e.g., erlotinib, panitumumab, cetuximab, nimotuzumab); HER2/neu receptor inhibitor (e.g., trastuzumab); dual kinase inhibitor (e.g., bosutinib, saracatinib, lapatinib, vandetanib); multikinase inhibitor (e.g., sorafenib, sunitinib, XL184, pazopanib); VEGF inhibitor (e.g., bevacizumab, AV-951, brivanib); radioimmunotherapy (e.g., XR303); cancer vaccine (e.g., GVAX, survivin peptide); COX-2 inhibitor (e.g., celecoxib); IGF-1 receptor inhibitor (e.g., AMG 479, MK-0646); mTOR inhibitor (e.g., everolimus, temsirolimus); IL-6 inhibitor (e.g., CNTO 328); cyclin-dependent kinase inhibitor (e.g., P276-00, UCN-01); Altered Energy Metabolism-Directed (AEMD) compound (e.g., CPI-613); HDAC inhibitor (e.g., vorinostat); TRAIL receptor 2 (TR-2) agonist (e.g., conatumumab); MEK inhibitor (e.g., AS703026, selumetinib, GSK1120212); Raf/MEK dual kinase inhibitor (e.g., RO5126766); Notch signaling inhibitor (e.g., MK0752); monoclonal antibody-antibody fusion protein (e.g., L19IL2); curcumin; HSP90 inhibitor (e.g., tanespimycin, STA-9090); riL-2; denileukin diftitox; topoisomerase 1 inhibitor (e.g., irinotecan, PEPO2); statin (e.g., simvastatin); Factor VIIa inhibitor (e.g., PCI-27483); AKT inhibitor (e.g., RX-0201); hypoxia-activated prodrug (e.g., TH-302); metformin hydrochloride, gamma-secretase inhibitor (e.g., RO4929097); ribonucleotide reductase inhibitor (e.g., 3-AP); immunotoxin (e.g., HuC242-DM4); PARP inhibitor (e.g., KU-0059436, veliparib); CTLA-4 inhibitor (e.g., CP-675,206, ipilimumab); AdVtk therapy; proteasome inhibitor (e.g., bortezomib (Velcade), NPI-0052); thiazolidinedione (e.g., pioglitazone); NPC-1C; Aurora kinase inhibitor (e.g., R763/AS703569), CTGF inhibitor (e.g., FG-3019); siG 12D LODER; and radiation therapy (e.g., tomotherapy, stereotactic radiation, proton therapy), surgery, and a combination thereof.

Small Cell Lung Cancer

Exemplary agents that that can be used conjointly with compounds disclosed herein to treat small cell lung cancer include, but are not limited to, etoposide, carboplatin, cisplatin, irinotecan, topotecan, gemcitabine, liposomal SN-38, bendamustine, temozolomide, belotecan, NK012, FR901228, flavopiridol); tyrosine kinase inhibitor (e.g., EGFR inhibitor (e.g., erlotinib, gefitinib, cetuximab, panitumumab); multikinase inhibitor (e.g., sorafenib, sunitinib); VEGF inhibitor (e.g., bevacizumab, vandetanib); cancer vaccine (e.g., GVAX); Bcl-2 inhibitor (e.g., oblimersen sodium, ABT-263), proteasome inhibitor (e.g., bortezomib (Velcade), NPI-0052); paclitaxel or a paclitaxel agent; docetaxel; IGF-1 receptor inhibitor (e.g., AMG 479); HGF/SF inhibitor (e.g., AMG 102, MK-0646); chloroquine; Aurora kinase inhibitor (e.g., MLN8237); radioimmunotherapy (e.g., TF2); HSP90 inhibitor (e.g., tanespimycin, STA-9090); mTOR inhibitor (e.g., everolimus); Ep-CAM-/CD3-bispecific antibody (e.g., MT110); CK-2 inhibitor (e.g., CX-4945); HDAC inhibitor (e.g., belinostat); SMO antagonist (e.g., BMS833923); peptide cancer vaccine, and radiation therapy (e.g., intensity-modulated radiation therapy (IMRT), hypofractionated radiotherapy, hypoxia-guided radiotherapy), surgery, and combinations thereof.

Non-Small Cell Lung Cancer

Exemplary agents that that can be used conjointly with compounds disclosed herein to treat non-small cell lung cancer include, but are not limited to, vinorelbine, cisplatin, docetaxel, pemetrexed disodium, etoposide, gemcitabine, carboplatin, liposomal SN-38, TLK286, temozolomide, topotecan, pemetrexed disodium, azacitidine, irinotecan, tegafurgimeracil-oteracil potassium, sapacitabine); tyrosine kinase inhibitor (e.g., EGFR inhibitor (e.g., erlotinib, gefitinib, cetuximab, panitumumab, necitumumab, PF-00299804, nimotuzumab, RO5083945), MET inhibitor (e.g., PF-02341066, ARQ 197), PI3K kinase inhibitor (e.g., XL147, GDC-0941), Raf/MEK dual kinase inhibitor (e.g., RO5126766), PI3K/mTOR dual kinase inhibitor (e.g., XL765), SRC inhibitor (e.g., dasatinib), dual inhibitor (e.g., BIBW 2992, GSK1363089, ZD6474, AZD0530, AG-013736, lapatinib, MEHD7945A, linifanib), multikinase inhibitor (e.g., sorafenib, sunitinib, pazopanib, AMG 706, XL184, MGCD265, BMS-690514, R935788), VEGF inhibitor (e.g., endostar, endostatin, bevacizumab, cediranib, BIBF 1120, axitinib, tivozanib, AZD2171), cancer vaccine (e.g., BLP25liposome vaccine, GVAX, recombinant DNA and adenovirus expressing L523S protein), Bcl-2 inhibitor (e.g., oblimersen, sodium), proteasome inhibitor (e.g., bortezomib, carfilzomib, NPI-0052, ixazomid), paclitaxel or a paclitaxel agent, docetaxel, IGF-1 receptor inhibitor (e.g., cixutumumab, MK-0646, OSI906, CP-751,871, BIIB022), hydroxychloroquine, HSP90 inhibitor (e.g., tanespimycin, STA-9090, AUY922, XL888), mTOR inhibitor (e.g., everolimus, temsirolimus, ridaforolimus), Ep-CAM-/CD3-bispecific antibody (e.g., MT110), CK-2 inhibitor (e.g., CX-4945), HDAC inhibitor (e.g., MS 275, LBH589, vorinostat, valproic acid, FR901228), DHFR inhibitor (e.g., pralatrexate), retinoid (e.g., bexarotene, tretinoin), antibody-drug conjugate (e.g., SGN-15), bisphosphonate (e.g., zoledronic acid), cancer vaccine (e.g., belagenpumatucel-L), low molecular weight heparin (LMWH) (e.g., tinzaparin, enoxaparin), GSK1572932A, melatonin, talactoferrin, dimesna, topoisomerase inhibitor (e.g., amrubicin, etoposide, karenitecin), nelfinavir, cilengitide, ErbB3 inhibitor (e.g., MM-121, U3-1287), survivin inhibitor (e.g., YM155, LY2181308), eribulin mesylate, COX-2 inhibitor (e.g., celecoxib), pegfilgrastim, Polo-like kinase 1 inhibitor (e.g., BI 6727), TRAIL receptor 2 (TR-2) agonist (e.g., CS-1008), CNGRC peptide-TNF alpha conjugate, dichloroacetate (DCA), HGF inhibitor (e.g., SCH 900105, SAR240550, PPAR-gamma agonist (e.g., CS-7017), gamma-secretase inhibitor (e.g., RO4929097), epigenetic therapy (e.g., 5-azacitidine), nitroglycerin, MEK inhibitor (e.g., AZD6244), cyclin-dependent kinase inhibitor (e.g., UCN-01), cholesterol-Fus1, antitubulin agent (e.g., E7389), farnesyl-OHtransferase inhibitor (e.g., lonafarnib), immunotoxin (e.g., BB-10901, SS1 (dsFv) PE38), fondaparinux, vascular-disrupting agent (e.g., A VE8062), PD-L1 inhibitor (e.g., MDX-1105, MDX-1106), beta-glucan, NGR-hTNF, EMD 521873, MEK inhibitor (e.g., GSK1120212), epothilone analog (e.g., ixabepilone), kinesin-spindle inhibitor (e.g., 4SC-205), telomere targeting agent (e.g., KML-001), P70 pathway inhibitor (e.g., LY2584702), AKT inhibitor (e.g., MK-2206), angiogenesis inhibitor (e.g., lenalidomide), Notch signaling inhibitor (e.g., OMP-21M18), radiation therapy, surgery, and combinations thereof.

Ovarian Cancer

Exemplary agents that that can be used conjointly with compounds disclosed herein to treat ovarian cancer include, but are not limited to, a chemotherapeutic agent (e.g., paclitaxel or a paclitaxel agent; docetaxel; carboplatin; gemcitabine; doxorubicin; topotecan; cisplatin; irinotecan, TLK286, ifosfamide, olaparib, oxaliplatin, melphalan, pemetrexed disodium, SJG-136, cyclophosphamide, etoposide, decitabine); ghrelin antagonist (e.g., AEZS-130), immunotherapy (e.g., APC8024, oregovomab, OPT-821), tyrosine kinase inhibitor (e.g., EGFR inhibitor (e.g., erlotinib), dual inhibitor (e.g., E7080), multikinase inhibitor (e.g., AZD0530, JI-101, sorafenib, sunitinib, pazopanib), ON 01910.Na), VEGF inhibitor (e.g., bevacizumab, BIBF 1120, cediranib, AZD2171), PDGFR inhibitor (e.g., IMC-303), paclitaxel, topoisomerase inhibitor (e.g., karenitecin, Irinotecan), HDAC inhibitor (e.g., valproate, vorinostat), folate receptor inhibitor (e.g., farletuzumab), angiopoietin inhibitor (e.g., AMG 386), epothilone analog (e.g., ixabepilone), proteasome inhibitor (e.g., carfilzomib), IGF-1 receptor inhibitor (e.g., OSI 906, AMG 479), PARP inhibitor (e.g., veliparib, AG014699, iniparib, MK-4827), Aurora kinase inhibitor (e.g., MLN8237, ENMD-2076), angiogenesis inhibitor (e.g., lenalidomide), DHFR inhibitor (e.g., pralatrexate), radioimmunotherapeutic agnet (e.g., Hu3S 193), statin (e.g., lovastatin), topoisomerase 1 inhibitor (e.g., NKTR-1 02), cancer vaccine (e.g., p53 synthetic long peptides vaccine, autologous OC-DC vaccine), mTOR inhibitor (e.g., temsirolimus, everolimus), BCR/ABL inhibitor (e.g., imatinib), ET-A receptor antagonist (e.g., ZD4054), TRAIL receptor 2 (TR-2) agonist (e.g., CS-1008), HGF/SF inhibitor (e.g., AMG 102), EGEN-001, Polo-like kinase 1 inhibitor (e.g., BI 6727), gamma-secretase inhibitor (e.g., RO4929097), Wee-1 inhibitor (e.g., MK-1775), antitubulin agent (e.g., vinorelbine, E7389), immunotoxin (e.g., denileukin diftitox), SB-485232, vascular-disrupting agent (e.g., A VE8062), integrin inhibitor (e.g., EMD 525797), kinesin-spindle inhibitor (e.g., 4SC-205), revlimid, HER2 inhibitor (e.g., MGAH22), ErrB3 inhibitor (e.g., MM-121), radiation therapy; and combinations thereof.

Myeloma

Exemplary agents that that can be conjointly administered with compounds disclosed herein to treat myeloma include, but are not limited to, thalidomide analogs, (e.g., lenalidomide), HSCT (Cook, R. (2008) J Manag Care Pharm. 14(7 Suppl):19-25), an anti-TIM-3 antibody (Hallett, W H D et al. (2011) J of American Society for Blood and Marrow Transplantation 17 (8): 1133-145), tumor antigen-pulsed dendritic cells, fusions (e.g., electrofusions) of tumor cells and dendritic cells, or vaccination with immunoglobulin idiotype produced by malignant plasma cells (reviewed in Yi, Q. (2009) Cancer J. 15(6):502-10).

Renal Cell Carcinoma

Exemplary agents that that can be conjointly administered with compounds disclosed herein to treat renal cell carcinoma include, but are not limited to, interleukin-2 or interferon-α, a targeted agent (e.g., a VEGF inhibitor such as a monoclonal antibody to VEGF, e.g., bevacizumab (Rini, B. I. et al. (2010) J. Clin. Oncol. 28(13):2137-2143)); a VEGF tyrosine kinase inhibitor such as sunitinib, sorafenib, axitinib and pazopanib (reviewed in Pal S. K. et al. (2014) Clin. Advances in Hematology & Oncology 12(2):90-99)); an RNAi inhibitor), or an inhibitor of a downstream mediator of VEGF signaling, e.g., an inhibitor of the mammalian target of rapamycin (mTOR), e.g., everolimus and temsirolimus (Hudes, G. et al. (2007) N. Engl. J. Med. 356(22): 2271-2281, Motzer, R. J. et al. (2008) Lancet 372: 449-456).

Chronic Myelogenous Leukemia

Exemplary agents that that can be conjointly administered with compounds disclosed herein to treat chronic myelogenous leukemia (CML) include, but are not limited to, a chemotherapeutic (e.g., cytarabine, hydroxyurea, clofarabine, melphalan, thiotepa, fludarabine, busulfan, etoposide, cordycepin, pentostatin, capecitabine, azacitidine, cyclophosphamide, cladribine, topotecan), tyrosine kinase inhibitor (e.g., BCR/ABL inhibitor (e.g., imatinib, nilotinib), a dual inhibitor (e.g., dasatinib, bosutinib), multikinase inhibitor (e.g., DCC-2036, ponatinib, sorafenib, sunitinib, RGB-286638)), interferon alfa, steroids, apoptotic agent (e.g., omacetaxine mepesuccinat), immunotherapy (e.g., allogeneic CD4+ memory Th1-like T cells/microparticle-bound anti-CD3/anti-CD28, autologous cytokine induced killer cells (CIK), AHN-12), CD52 targeting agent (e.g., alemtuzumab), HSP90 inhibitor (e.g., tanespimycin, STA-9090, AUY922, XL888), mTOR inhibitor (e.g., everolimus), SMO antagonist (e.g., BMS 833923), ribonucleotide reductase inhibitor (e.g., 3-AP), JAK-2 inhibitor (e.g., INCB018424), hydroxychloroquine, retinoid (e.g., fenretinide), cyclin-dependent kinase inhibitor (e.g., UCN-01), HDAC inhibitor (e.g., belinostat, vorinostat, JNJ-26481585), PARP inhibitor (e.g., veliparib), MDM2 antagonist (e.g., RO5045337), Aurora B kinase inhibitor (e.g., TAK-901), radioimmunotherapy (e.g., actinium-225-labeled anti-CD33 antibody HuM195), Hedgehog inhibitor (e.g., PF-04449913), STAT3 inhibitor (e.g., OPB-31121), KB004, cancer vaccine (e.g., AG858), bone marrow transplantation, stem cell transplantation, radiation therapy, and combinations thereof.

Chronic Lymphocyic Leukemia

Exemplary agents that that can be conjointly administered with compounds disclosed herein to treat chronic lymphocyic leukemia (CLL) include, but are not limited to, a chemotherapeutic agent (e.g., fludarabine, cyclophosphamide, doxorubicin, vincristine, chlorambucil, bendamustine, chlorambucil, busulfan, gemcitabine, melphalan, pentostatin, mitoxantrone, 5-azacytidine, pemetrexed disodium), tyrosine kinase inhibitor (e.g., EGFR inhibitor (e.g., erlotinib), BTK inhibitor (e.g., PCI-32765), multikinase inhibitor (e.g., MGCD265, RGB-286638), CD-20 targeting agent (e.g., rituximab, ofatumumab, RO5072759, LFB-R603), CD52 targeting agent (e.g., alemtuzumab), prednisolone, darbepoetin alfa, lenalidomide, Bcl-2 inhibitor (e.g., ABT-263), immunotherapy (e.g., allogeneic CD4+ memory Th1-like T cells/microparticle-bound anti-CD3/anti-CD28, autologous cytokine induced killer cells (CIK)), HDAC inhibitor (e.g., vorinostat, valproic acid, LBH589, JNJ-26481585, AR-42), XIAP inhibitor (e.g., AEG35156), CD-74 targeting agent (e.g., milatuzumab), mTOR inhibitor (e.g., everolimus), AT-101, immunotoxin (e.g., CAT-8015, anti-Tac(Fv)-PE38 (LMB-2)), CD37 targeting agent (e.g., TRU-5016), radioimmunotherapy (e.g., 131-tositumomab), hydroxychloroquine, perifosine, SRC inhibitor (e.g., dasatinib), thalidomide, PI3K delta inhibitor (e.g., CAL-101), retinoid (e.g., fenretinide), MDM2 antagonist (e.g., RO5045337), plerixafor, Aurora kinase inhibitor (e.g., MLN8237, TAK-901), proteasome inhibitor (e.g., bortezomib), CD-19 targeting agent (e.g., MEDI-551, MOR208), MEK inhibitor (e.g., ABT-348), JAK-2 inhibitor (e.g., INCB018424), hypoxia-activated prodrug (e.g., TH-302), paclitaxel or a paclitaxel agent, HSP90 inhibitor, AKT inhibitor (e.g., MK2206), HMG-CoA inhibitor (e.g., simvastatin), GNKG 186, radiation therapy, bone marrow transplantation, stem cell transplantation, and combinations thereof.

Acute lymphocyic leukemia Exemplary agents that that can be conjointly administered with compounds disclosed herein to treat acute lymphocyic leukemia (ALL) include, but are not limited to, a chemotherapeutic agent (e.g., prednisolone, dexamethasone, vincristine, asparaginase, daunorubicin, cyclophosphamide, cytarabine, etoposide, thioguanine, mercaptopurine, clofarabine, liposomal annamycin, busulfan, etoposide, capecitabine, decitabine, azacitidine, topotecan, temozolomide), tyrosine kinase inhibitor (e.g., BCR/ABL inhibitor (e.g., imatinib, nilotinib), ON 01910.Na, multikinase inhibitor (e.g., sorafenib)), CD-20 targeting agent (e.g., rituximab), CD52 targeting agent (e.g., alemtuzumab), HSP90 inhibitor (e.g., STA-9090), mTOR inhibitor (e.g., everolimus, rapamycin), JAK-2 inhibitor (e.g., INCB018424), HER2/neu receptor inhibitor (e.g., trastuzumab), proteasome inhibitor (e.g., bortezomib), methotrexate, asparaginase, CD-22 targeting agent (e.g., epratuzumab, inotuzumab), immunotherapy (e.g., autologous cytokine induced killer cells (CIK), AHN-12), blinatumomab, cyclin-dependent kinase inhibitor (e.g., UCN-01), CD45 targeting agent (e.g., BC8), MDM2 antagonist (e.g., RO5045337), immunotoxin (e.g., CAT-8015, DT2219ARL), HDAC inhibitor (e.g., JNJ-26481585), JVRS-100, paclitaxel or a paclitaxel agent, STAT3 inhibitor (e.g., OPB-31121), PARP inhibitor (e.g., veliparib), EZN-2285, bone marrow transplantation, stem cell transplantation, radiation therapy, and combinations thereof.

Acute Myeloid Leukemia

Exemplary agents that that can be conjointly administered with compounds disclosed herein to treat acute myeloid leukemia (AML) include, but are not limited to, a chemotherapeutic agent (e.g., cytarabine, daunorubicin, idarubicin, clofarabine, decitabine, vosaroxin, azacitidine, clofarabine, ribavirin, CPX-351, treosulfan, elacytarabine, azacitidine), tyrosine kinase inhibitor (e.g., BCR/ABL inhibitor (e.g., imatinib, nilotinib), ON 01910.Na, multikinase inhibitor (e.g., midostaurin, SU 11248, quizartinib, sorafinib)), immunotoxin (e.g., gemtuzumab ozogamicin), DT388IL3 fusion protein, HDAC inhibitor (e.g., vorinostat, LBH589), plerixafor, mTOR inhibitor (e.g., everolimus), SRC inhibitor (e.g., dasatinib), HSP90 inhibitor (e.g., STA-9090), retinoid (e.g., bexarotene, Aurora kinase inhibitor (e.g., BI 811283), JAK-2 inhibitor (e.g., INCB018424), Polo-like kinase inhibitor (e.g., BI 6727), cenersen, CD45 targeting agent (e.g., BC8), cyclin-dependent kinase inhibitor (e.g., UCN-01), MDM2 antagonist (e.g., R05045337), mTOR inhibitor (e.g., everolimus), LY573636-sodium, ZRx-101, MLN4924, lenalidomide, immunotherapy (e.g., AHN-12), histamine dihydrochloride, bone marrow transplantation, stem cell transplantation, radiation therapy, and combinations thereof.

Multiple Myeloma

Exemplary agents that can be conjointly administered with compounds disclosed herein to treat multiple myeloma include, but are not limited to, a chemotherapeutic agent (e.g., melphalan, amifostine, cyclophosphamide, doxorubicin, clofarabine, bendamustine, fludarabine, adriamycin, SyB L-0501), thalidomide, lenalidomide, dexamethasone, prednisone, pomalidomide, proteasome inhibitor (e.g., bortezomib, carfilzomib, ixazomid), cancer vaccine (e.g., GVAX), CD-40 targeting agent (e.g., SGN-40, CHIR-12.12), perifosine, zoledronic acid, immunotherapy (e.g., MAGE-A3, NY-ESO-1, HuMax-CD38), HDAC inhibitor (e.g., vorinostat, LBH589, AR-42), aplidin, cycline-dependent kinase inhibitor (e.g., PD-0332991, dinaciclib), arsenic trioxide, CB3304, HSP90 inhibitor (e.g., KW-2478), tyrosine kinase inhibitor (e.g., EGFR inhibitor (e.g., cetuximab), multikinase inhibitor (e.g., AT9283)), VEGF inhibitor (e.g., bevacizumab), plerixafor, MEK inhibitor (e.g., AZD6244), IPH2101, atorvastatin, immunotoxin (e.g., BB-10901), NPI-0052, radioimmunotherapeutic (e.g., yttrium Y 90 ibritumomab tiuxetan), STAT3 inhibitor (e.g., OPB-31121), MLN4924, Aurora kinase inhibitor (e.g., ENMD-2076), IMGN901, ACE-041, CK-2 inhibitor (e.g., CX-4945), bone marrow transplantation, stem cell transplantation, radiation therapy, and combinations thereof.

Prostate Cancer

Exemplary agents that can be conjointly administered with compounds disclosed herein to treat prostate cancer include, but are not limited to, a chemotherapeutic agent (e.g., docetaxel, carboplatin, fludarabine), abiraterone, hormonal therapy (e.g., flutamide, bicalutamide, nilutamide, cyproterone acetate, ketoconazole, aminoglutethimide, abarelix, degarelix, leuprolide, goserelin, triptorelin, buserelin), tyrosine kinase inhibitor (e.g., dual kinase inhibitor (e.g., lapatanib), multikinase inhibitor (e.g., sorafenib, sunitinib)), VEGF inhibitor (e.g., bevacizumab), TAK-700, cancer vaccine (e.g., BPX-101, PEP223), lenalidomide, TOK-001, IGF-1 receptor inhibitor (e.g., cixutumumab), TRC105, Aurora A kinase inhibitor (e.g., MLN8237), proteasome inhibitor (e.g., bortezomib), OGX-011, radioimmunotherapy (e.g., HuJ591-GS), HDAC inhibitor (e.g., valproic acid, SB939, LBH589), hydroxychloroquine, mTOR inhibitor (e.g., everolimus), dovitinib lactate, diindolylmethane, efavirenz, OGX-427, genistein, IMC-303, bafetinib, CP-675,206, radiation therapy, surgery, or a combination thereof.

Hodgkin's Lymphomas

Exemplary agents that that can be used conjointly with compounds disclosed herein for the treatment of Hodgkin's lymphomas include, but are not limited to, chemotherapeutics such as Doxorubicin (Adriamycin), bleomycin (Blenoxane), vinblastine (Velban, Velsar), dacarbazine, etoposide (Toposar, VePesid), cyclophosphamide (Cytoxan, Neosar), vincristine (Vincasar PFS, Oncovin), procarbazine (Matulane), prednisone, Ifosfamide (Ifex), carboplatin (Paraplatin), Mechlorethamine, Chlorambucil, methylprenisolone (Solu-Medrol), cytarabine (Cytosar-U), cisplatin (Platinol), Gemcitabine (Gemzar), vinorelbine (Navelbine), oxaliplatin (Eloxatin), Lomustine, Mitoxantrone, carmustine, melphalan, Bendamustine, Lenalidomide, and vinorelbine; either alone or in combinations; Brentuximab vedotin (Adcetris—a CD30 anti-body drug conjugate); Iodine131-CHT25 antibody conjugate; HDAC inhibitors (e.g., vorinostat); m-TOR inhibitors (e.g., everolimus, temsirolimus); PI3K inhibitors (e.g., CAL-101, BAY80-6946, TGR-1202, BKM-120, AMG-319); JAK/STAT pathway inhibitors; Bcl-2 inhibitors (e.g., venetoclax); Mcl-1 inhibitors; multi-kinase inhibitors such as BAY 43-9006 (sorafenib); proteasome inhibitors (e.g., bortezomib (Velcade), NPI-0052); dual PI3K/HDAC targeted inhibitors (e.g., CUDC-907); NF-kB inhibitors; anti-PD-1 antibodies (e.g., nivolumab, pembrolizumab); anti-CTLA-4 antibodies (e.g., ipilimumab); anti-CD-20 antibodies (e.g., rituximab); anti-CD40 antibodies; anti-CD80 antibodies; and radiation therapy (e.g., tomotherapy, stereotactic radiation, proton therapy), surgery, and a combination thereof.

Non-Hodgkin's Lymphomas

Exemplary agents that that can be used conjointly with compounds disclosed herein for the treatment of Hodgkin's lymphomas include, but are not limited to, chemotherapeutics such as Doxorubicin (Adriamycin), bleomycin (Blenoxane), vinblastine (Velban, Velsar), dacarbazine, etoposide (Toposar, VePesid), cyclophosphamide (Cytoxan, Neosar), vincristine (Vincasar PFS, Oncovin), procarbazine (Matulane), prednisone, Ifosfamide (Ifex), carboplatin (Paraplatin), Mechlorethamine, Chlorambucil, methylprenisolone (Solu-Medrol), cytarabine (Cytosar-U), cisplatin (Platinol), Gemcitabine (Gemzar), vinorelbine (Navelbine), oxaliplatin (Eloxatin), Lomustine, Mitoxantrone, methotrexate, carmustine, melphalan, Bendamustine, Lenalidomide, and vinorelbine; either alone or in combinations; tyrosine kinase inhibitors (e.g., EGFR inhibitor (e.g., erlotinib, panitumumab, cetuximab, nimotuzumab); HDAC inhibitors (e.g., vorinostat); IRAK-4 inhibitors; HSP90 inhibitors (e.g., tanespimycin, STA-9090, CUDC-305); m-TOR inhibitors (e.g., everolimus, temsirolimus); PI3K inhibitors (e.g., CAL-101, BAY80-6946, TGR-1202, BKM-120, AMG-319); JAK/STAT pathway inhibitors; AKT inhibitors (e.g., RX-0201); Bcl-2 inhibitors (e.g., venetoclax); Mcl-1 inhibitors; multikinase inhibitors such as BAY 43-9006 (sorafenib); proteasome inhibitors (e.g., bortezomib (Velcade), NPI-0052); dual PI3K/HDAC targeted inhibitors (e.g., CUDC-907); NF-kB inhibitors; BTK inhibitors (e.g., ibrutinib); BET bromodomain inhibitors; anti-PD-1 antibodies (e.g., nivolumab, pembrolizumab); anti-CTLA-4 antibodies (e.g., ipilimumab); anti-CD-20 antibodies (e.g., rituximab); anti-CD40 antibodies; anti-CD80 antibodies; and radiation therapy (e.g., tomotherapy, stereotactic radiation, proton therapy), surgery, and a combination thereof.

In certain embodiments, a compound of Formula (I) of the disclosure may be conjointly administered with non-chemical methods of cancer treatment. In a further embodiment, a compound of Formula (I) of the disclosure may be conjointly administered with radiation therapy. In a further embodiment, a compound of Formula (I) of the disclosure may be conjointly administered with surgery, with thermoablation, with focused ultrasound therapy, with cryotherapy, or with any combination of these.

In certain embodiments, different compounds of the disclosure may be conjointly administered with one or more other compounds of the disclosure. Moreover, such combinations may be conjointly administered with other therapeutic agents, such as other agents suitable for the treatment of cancer, immunological or neurological diseases, such as the agents identified above. In certain embodiments, conjointly administering one or more additional chemotherapeutic agents with a compound of Formula (I) of the disclosure provides a synergistic effect. In certain embodiments, conjointly administering one or more additional chemotherapeutics agents provides an additive effect.

Pharmaceutical Compositions

In certain embodiments, the present disclosure provides a pharmaceutical composition comprising a compound of Formula (I) as disclosed herein, optionally admixed with a pharmaceutically acceptable carrier or diluent.

The present disclosure also provides methods for formulating the disclosed compounds of Formula (I) for pharmaceutical administration.

The compositions and methods of the present disclosure may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of Formula (I) of the disclosure and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of Formula (I) of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of Formula (I) of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect.

Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of Formula (I) of the disclosure, with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this disclosure. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference in its entirety. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

A suppository also is contemplated as being within the scope of this disclosure.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this disclosure, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required.

For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of Formula (I) of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions and Abbreviations:

Unless defined otherwise, all technical and scientific terms used herein have the same meaning and the meaning of such terms is independent at each occurrence thereof and is as commonly understood by one of skill in art to which the subject matter herein belongs. That notwithstanding and except where stated otherwise, the following definitions apply throughout the specification and claims. Chemical names, common names and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

The term "compound(s) of the present invention", unless otherwise specifically stated, comprises compounds of formula (I) or formula (IA) or formula (IB) or a pharmaceutical acceptable salt thereof and stereoisomers thereof.

As used herein, the terms "optional" or "optionally" mean that the subsequently described event or circumstance may occur or may not occur and that the description includes instances where the event or circumstance occurs as well as instances in which it does not. For example, "optionally substituted alkyl" refers to the event or circumstance where alkyl is substituted as well as the event or circumstance where the alkyl is not substituted.

The term "substituted", unless the substituents are specifically mentioned, refers to moieties having substituents replacing hydrogen on one or more carbons of the backbone. It will be understood that "substitution" or "substituted with" includes the implicit proviso that such substitution is in accordance with permitted valence of the substituted atom and the substituent and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxyl, an oxo, an amino, an amido, an amidine, a nitro, an azido, a heteroaryl, an aralkyl or an aromatic or heteroaromatic moiety. It will be understood by those skilled in the art that substituents can themselves be substituted, if appropriate.

As used herein, the term "alkyl" refers to saturated aliphatic groups, including but not limited to $C_1$-$C_{10}$ straight-chain alkyl groups or $C_3$-$C_{10}$ branched-chain alkyl groups. Preferably, the "alkyl" group refers to $C_1$-$C_6$ straight-chain alkyl groups or $C_3$-$C_6$ branched-chain alkyl groups. Most preferably, the "alkyl" group refers to $C_1$-$C_4$ straight-chain alkyl groups or $C_3$-$C_8$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl and 4-octyl. The "alkyl" group may be optionally substituted.

The term "aryl" as used herein include substituted or unsubstituted single-ring aromatic groups in which each atom of the ring is carbon. Preferably the ring is a 5- to 7-membered ring, more preferably a 6-membered ring. Particularly, the term 'aryl' includes phenyl.

As used herein, the expression "(p-OH)aryl" means aryl group which is para-substituted with hydroxyl (—OH) group, wherein the aryl group is as defined above.

The term "heteroaryl" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. Particularly, the term 'heteroaryl' includes imidazole. A heteroaryl group may be substituted at one or more positions, as permitted by valence, with any optional substituents described herein.

As used herein, the term "aralkyl" includes an aryl group substituted with alkyl radical(s) by replacing one or more hydrogen atom(s).

As used herein, the term "including" as well as other forms, such as "include", "includes," and "included," is not limiting.

Throughout this specification and claims, the 'L-threonine residue' structurally mentioned in compounds of the present invention and/or preparation thereof can be represented by any one of the following formulae. This representation may be interpreted to other compounds having similar structural motifs.

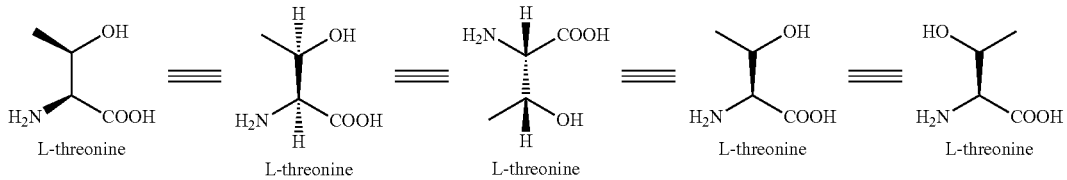

As used herein, the term "aryloxy" refers to the group —O-aryl, where aryl group is as defined above.

As used herein, the term "heteroarylalkyl" refers to a alkyl group, attached to heteroaryl group, wherein 'alkyl' and 'heteroaryl' groups are as defined above.

As used herein, a therapeutic that "prevents" a disorder or condition refers to a compound that, in a statistical sample, reduces the occurrence of the disorder or condition in the treated sample relative to an untreated control sample or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate or stabilize the existing unwanted condition or side effects thereof).

The term "prodrug" is intended to encompass compounds which, under physiologic conditions, are converted into the therapeutically active agents of the present invention (e.g., a compound of formula (I)). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula (I) in a formulation represented above can be replaced with the corresponding suitable prodrug, e.g., wherein a hydroxyl in the parent compound is presented as an ester or a carbonate or carboxylic acid present in the parent compound is presented as an ester.

As used herein, the term "comprise" or "comprising" is generally used in the sense of include, that is to say permitting the presence of one or more additional (unspecified) features or components.

This invention includes pharmaceutically acceptable salts of compounds of the invention and their use in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide and the like. Mixtures of such solvates can also be prepared. The source of such solvate can be from the solvent of crystallization, inherent in the solvent of preparation or crystallization or adventitious to such solvent.

The term "stereoisomers" refers to any enantiomers, diastereoisomers or geometrical isomers, such as of the compounds of the invention. When compounds of the invention are chiral, they can exist in racemic or in optically active form. Since the pharmaceutical activity of the racemates or stereoisomers of the compounds according to the invention may differ, it may be desirable to use compounds that are enriched in one of the enantiomers. In these cases, the end product or even the intermediates can be separated into enantiomeric compounds by chemical or physical measures known to the person skilled in the art or even employed as such in the synthesis. In the case of racemic amines, diastereomers are formed from the mixture by reaction with an optically active resolving agent. Examples of suitable resolving agents are optically active acids such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline) or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel).

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee or even 95% or greater ee. In certain embodiments, compounds of the invention may have more than one stereocenter. In certain such embodiments, compounds of the invention may be enriched in one or more diastereomer. For example, a compound of the invention may have greater than 30% de, 40% de, 50% de, 60% de, 70% de, 80% de, 90% de or even 95% or greater de.

The term "subject" includes mammals (especially humans) and other animals, such as domestic animals (e.g., household pets including cats and dogs) and non-domestic animals (such as wildlife).

The abbreviations used in the entire specification may be summarized herein below with their particular meaning.

° C. (degree Celsius); % (percentage); brine (NaCl solution); Boc (Tert-butyloxycarbonyl); DIC: N,N'-Diisopropylcarbodiimide; DIPEA (N,N-Diisopropylethylamine); DMF (Dimethyl formamide); EtOH (Ethanol); EtOAc (Ethyl Acetate); Fmoc (9-Fluorenylmethyloxycarbonyl); g or gr (gram); HOBt (1-Hydroxy benzotriazole); h or hr (Hours); HPLC (High-performance liquid chromatography); LCMS (Liquid chromatography mass spectroscopy); mmol (Millimoles); M (Molar); µl (Microlitre); mL (Millilitre); mg (Milligram); min (Minutes); NaHCO$_3$ (Sodium bicarbonate); NMM (N-Methylmorpholine); Na$_2$SO$_4$ (Sodium sulphate); NH$_2$OH·HCl (Hydroxylamine hydrochloride); prep-HPLC/preparative HPLC (Preparative High-performance liquid chromatography); TEA/Et$_3$N (Triethylamine); TLC (Thin Layer Chromatography); THF (Tetrahydrofuran); TIPS (Triisopropylsilane); t$_R$ (Retention time); etc.

EXPERIMENTAL

Analytical HPLC Methods:
Method-1: Hilic Method
  Column: ZIC-HILLIC (Sequant), C18 (4.6×250 mm, 5 µm) 200A°
  Flow: 1.0 mL/min; Column Temp: 25.0° C.
  Mobile phase: A=5 mM Ammonium Acetate PH-4.0 (Acetic Acid), B=ACN
  Gradient (Time/% B): 0/85, 2/85, 20/40, 20.1/85, 30/85.
Method 2: DiBoc Method
  Column: PhenomenexAeris peptide C18 (2) 100A (250× 4.6 mm, 3.6µ)
  Flow: 1.0 mL/min; Column Temp: 25.0° C.
  Mobile Phase: A=0.1% TFA (Aq), B=ACN
  Gradient (Time/% B): 0/2, 2/2, 15/70, 20/95, 25/100, 30/100, 32/2, 42/2
Preparative HPLC Method:
  Preparative HPLC was performed on SeQuant ZIC HILIC 200 A° column (10 mm×250 mm, 5 µm), Flow rate: 5.0 mL/min. The elution conditions used are: Buffer A: 5 mmol ammonium acetate (adjust to pH-4 with Acetic Acid), Buffer B: Acetonitrile, Equilibration of the column with 90% buffer B and elution by a gradient of 90% to 40% buffer B during 20 min.

LCMS was performed on AP1 2000 LC/MS/MS triple quad (Applied biosystems) with Agilent 1100 series HPLC with G1315 B DAD, using Mercury MS column or using Agilent LC/MSD VL single quad with Agilent 1100 series HPLC with G1315 B DAD, using Mercury MS column or using Shimadzu LCMS 2020 single quad with Prominence UFLC system with SPD-20 A DAD.

Example 1: ((S)-2-(3-((S)-1-amino-2-(4-hydroxyphenyl)ethyl)-1,2,4-oxadiazol-5-yl)pyrrolidine-1-carbonyl)-L-aspartic acid (Compound 1)

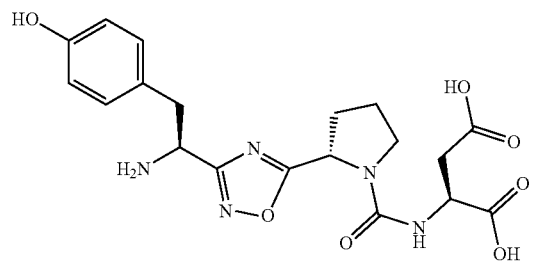 [SMILES: N[C@@H](Cc1ccc(O)cc1)c1noc([C@@H]2CCCN2C(=O)N[C@@H](CC(=O)O)C(=O)O)n1]

Step 1a: Synthesis of compound 1b

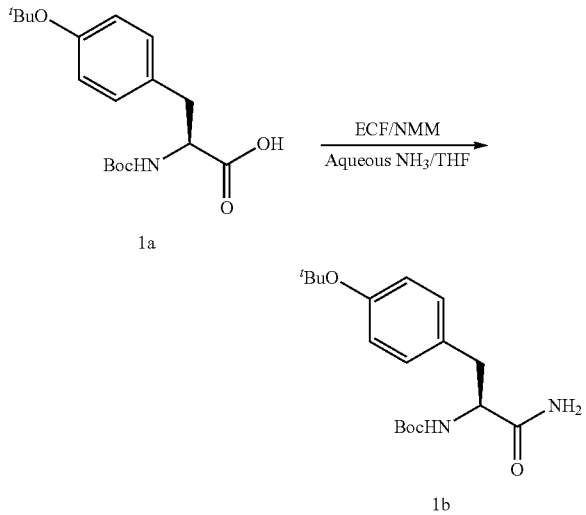

Ethylchloroformate (4.8 g, 44.4 mmol) and NMM (4.5 g, 44.4 mmol) were added to a solution of compound 1a (10.0 g, 29.63 mmol) in THF (120 mL) and stirred at −20° C. for 20 min. After 20 minutes, 25% of aqueous ammonia (30 mL) was added to the active mixed anhydride and stirred at 0-5° C. for 30 min. The completeness of the reaction was confirmed by TLC analysis. The volatiles were evaporated under reduced pressure and partitioned between water and ethyl acetate. The organic layer was washed with NaHCO$_3$ solution followed by citric acid solution and brine solution. The separated organic layer was dried over Na$_2$SO$_4$, filtered and evaporated under reduced pressure to yield 8.9 g of compound 1b. LCMS: 337.4 [M+H]$^+$.

Step 1b: Synthesis of compound 1c

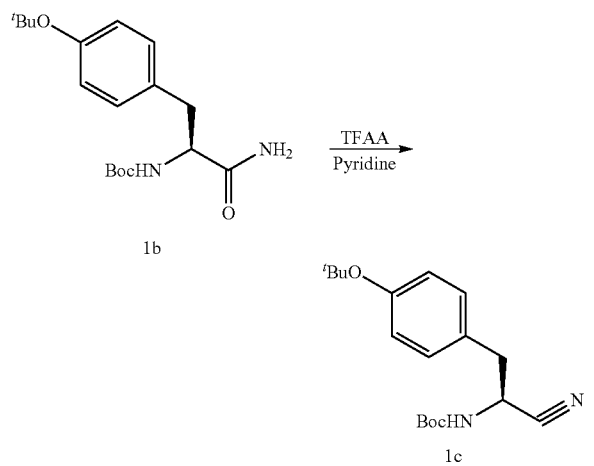

Trifluroacetic anhydride (TFAA) (14.2 g, 67.77 mmol) was added to a solution of compound 1b (7.6 g, 22.59 mmol) in pyridine (9.92 mL, 112.96 mmol) and stirred at room temperature for 2 h. The completion of the reaction was confirmed by TLC analysis. The volatiles were evaporated under reduced pressure and partitioned between water and ethyl acetate. The organic layer was washed with NaHCO₃ solution followed by citric acid and brine solution. The separated organic layer was dried over Na₂SO₄, filtered and evaporated under reduced pressure to yield 5.5 g of compound 1c, which was used for next step directly.

Step 1c: Synthesis of compound 1d

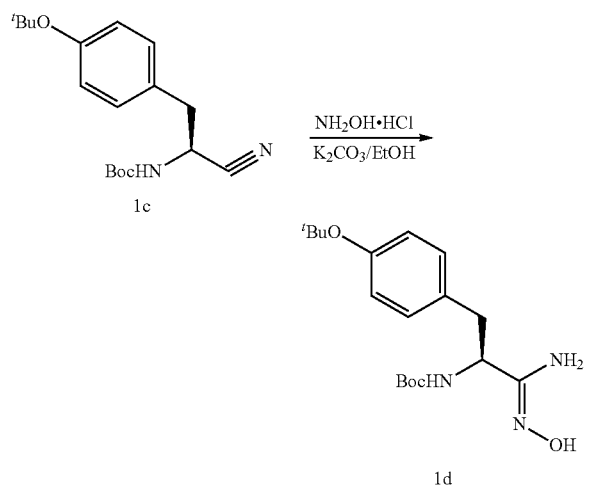

Hydroxylamine hydrochloride (1.62 g, 23.56 mmol), water (9.4 mL) and potassium carbonate (2.17 g, 15.7 mmol) were added to a solution of compound 1c (2.5 g, 7.8 mmol) in EtOH (28 mL) and stirred at 86° C. for 4 h. The completion of the reaction was confirmed by TLC analysis. The volatiles were evaporated under reduced pressure and partitioned between water and ethyl acetate. The organic layer was washed with brine solution, dried over Na₂SO₄ then filtered and evaporated under reduced pressure to yield 2.4 g of compound 1d. LCMS: 351.8 [M+H]⁺.

Step-1d: Synthesis of compound 1e

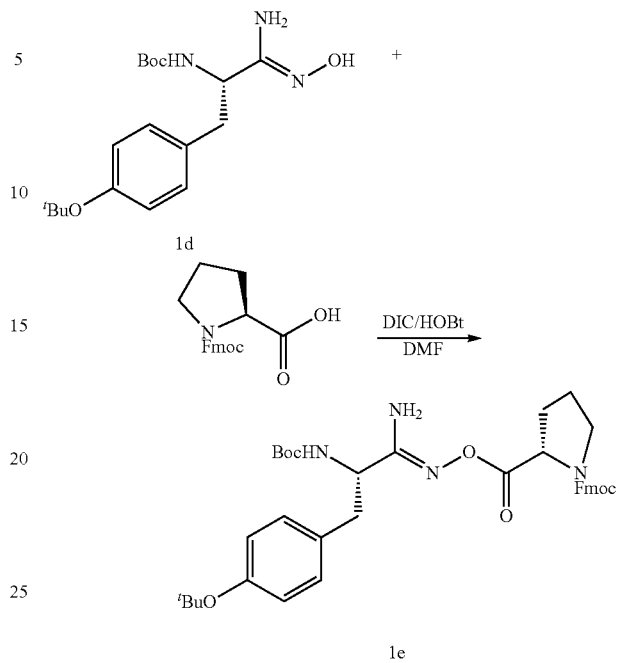

To a solution of Fmoc-Pro-OH (1.5 g, 4.5 mmol) in DMF (20 mL) were added HOBt (1.92 g, 14.23 mmol) and DIC (1.8 g, 14.23 mmol) at 0° C. and stirred for 15 min. Then compound 1d (2 g, 5.7 mmol) was added at the same temperature and continued stirring for 1 h and then at room temperature for 2 h. The completion of the reaction was confirmed by TLC analysis. The reaction mixture was quenched with ice water, the precipitated white solid was filtered, washed with water (150 mL) and dried under high reduced pressure. The solid was stirred with diethyl ether (250 mL) for 15 min, filtered and dried to yield 3.2 g of compound 1e. LCMS: 671.1 [M+H]⁺.

Step 1e: Synthesis of compound 1f

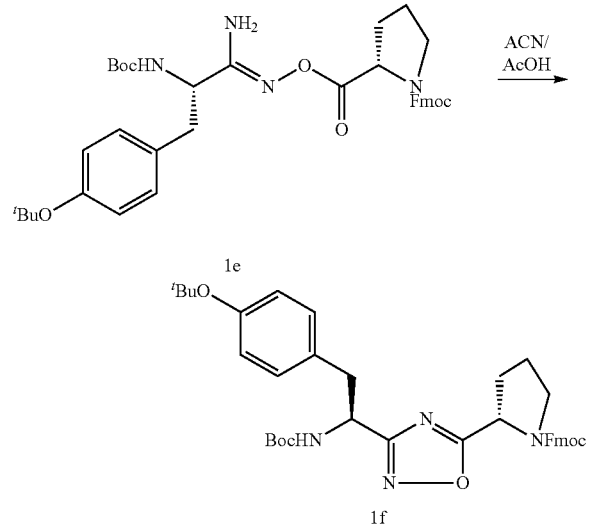

To a solution of compound 1e (3.2 g, 4.7 mmol) in acetonitrile (30 ml) was added acetic acid (3.2 mL) at room temperature and refluxed at 90° C. for 12 h. The completion of the reaction was confirmed by TLC analysis. The volatiles were evaporated under reduced pressure to obtain crude semi solid which was diluted with water and ethyl acetate. The organic layer was washed with NaHCO₃ solution followed by citric acid and brine solution. The organic layer was dried over Na₂SO₄, filtered and evaporated under reduced pressure to get crude solid which was diluted with 10% acetonitrile in hexane (50 ml) and stirred for 2 h to afford white solid. The obtained white solid was filtered and washed with n-pentane (50 mL) and dried to yield 0.9 g of compound if. LCMS: 653.4 [M+H]⁺.

Step 1f: Sythesis of compound 1g

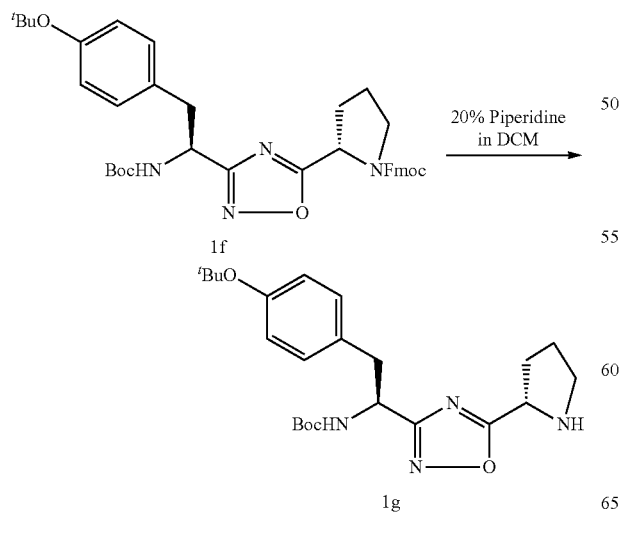

To a solution of 20% piperidine in DCM (15 mL) was added compound if (1.2 g, 1.83 mmol) at 0° C. and stirred at same temperature for 1 h. The completion of the reaction was confirmed by TLC analysis. The reaction mixture was concentrated under reduced pressure and diluted with hexane, stirred and filtered. The filtered solid was dissolved in EtOAc and washed with sat. NaHCO₃ solution, brine solution, dried over Na₂SO₄ filtered and evaporated to yield 0.65 g of compound 1g. LCMS 431.1 [M+H]⁺.

Step 1g: Synthesis of compound 1i

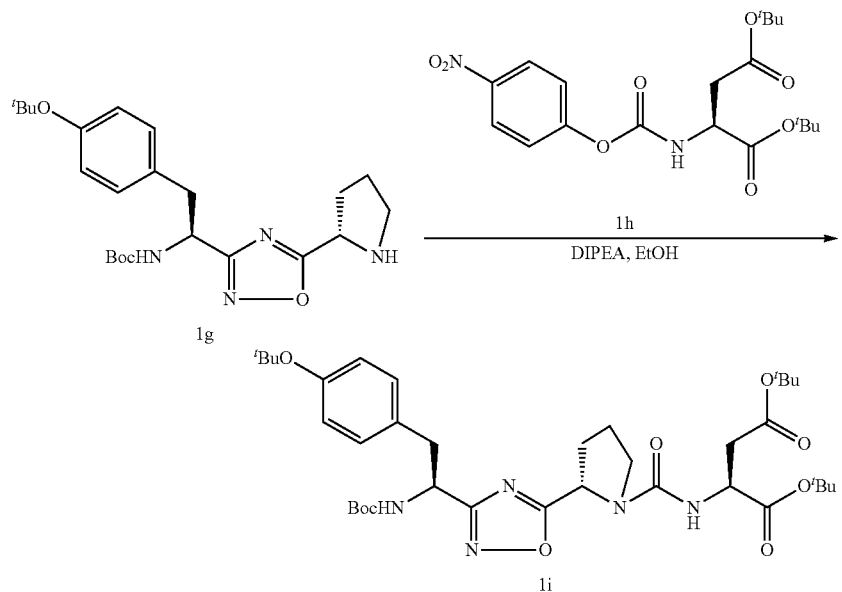

DIPEA (0.19 g, 1.5 mmol) was added to a solution of compound 1h (0.74 g, 1.81 mmol, prepared as per the procedure given below) and compound 1g (0.65 g, 1.5 mmol) in EtOH (10 mL) was stirred at RT for 3 h. The volatiles were evaporated and partitioned between ethyl acetate and water. The organic layer was washed with saturated NaHCO₃ 10% citric acid, brine solution, dried over Na₂SO₄ and concentrated under reduced pressure. The crude compound was purified by column chromatography over neutral alumina using 25% ethyl acetate in hexane to yield 0.75 g compound 1i. LCMS: 702.4 [M+H]⁺.

Step 1h: Synthesis of Compound 1

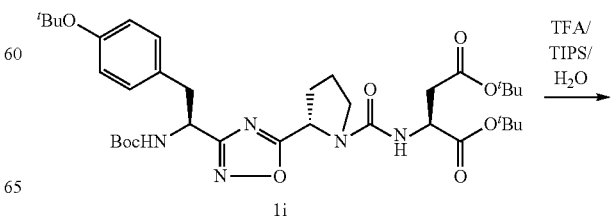

61

-continued

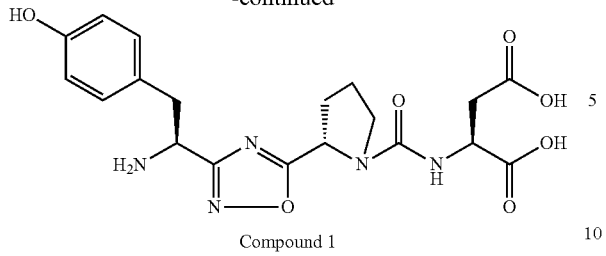

Compound 1

A solution of compound 1i (0.75 g, 1.06 mmol) was added 7.5 mL of cocktail mixture of and trifluoroacetic:TIPS:water (95:2.5:2.5) and was stirred at RT for 2 h. The resulting reaction mixture was evaporated under reduced pressure, diluted with diethyl ether and filtered to yield 0.4 g of crude compound 1. The crude solid material was purified by preparative HPLC method described under experimental conditions. LCMS: 434.3 [M+H]⁺. HPLC RT (min): 11.1

Synthesis of compound 1h

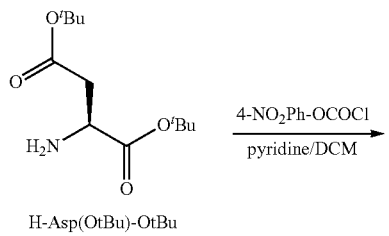

H-Asp(OtBu)-OtBu

62

-continued

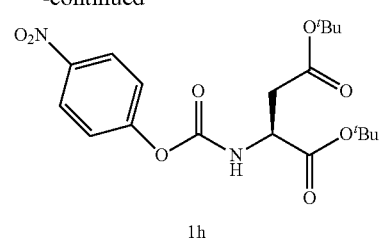

1h

To a solution of H-Asp(O^tBu)-O^tBu (1.0 g, 3.54 mmol) in CH$_2$Cl$_2$ (20 mL) was added pyridine (0.55 g, 7.08 mmol) and the solution was stirred at room temperature for 10 min. To this mixture was added a solution of 4-nitrophenyl chloroformate (0.86 g, 4.25 mmol) in CH$_2$Cl$_2$ (20 mL) and the resultant mixture was stirred at room temperature for 1 h. After completion of reaction (confirmed by TLC) it was diluted with CH$_2$Cl$_2$ (50 mL) and washed with 1.0 M of sodium bisulphate solution (50 mL×2) followed by 1.0 M sodium carbonate solution (50 mL×2). The organic layer was dried over Na$_2$SO$_4$, filtered and evaporated under reduced pressure to yield crude compound 1h, which was purified by silica gel column chromatography (eluent: 0-20% ethyl acetate in hexane) and yields 0.75 g of compound.

The below compounds were prepared by procedure similar to the one described in Example 1 (compound 1) with appropriate variations in reactants, quantities of reagents, solvents and reaction conditions. The characterization data of the compounds are summarized herein below table.

| Compound No. | Structure | HPLC ($t_R$ in min) Method 2 | LCMS [M + H]⁺ |
|---|---|---|---|
| 2 | 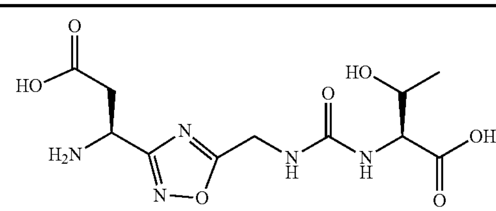 | 13.1 | 331.6 |
| 3 | 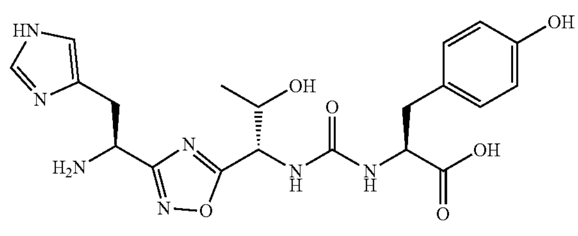 [SMILES: CC(O)[C@H](NC(=O)N[C@@H](Cc1ccc(O)cc1)C(=O)O)c1nc([C@@H](N)Cc2c[nH]cn2)no1] | 14.7 | 460.1 |
| 4 | 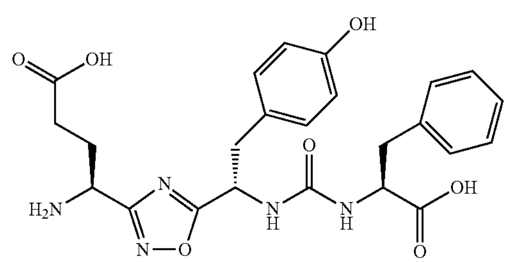 [SMILES: N[C@@H](CCC(=O)O)c1noc([C@H](Cc2ccc(O)cc2)NC(=O)N[C@@H](Cc2ccccc2)C(=O)O)n1] | 13.15 | 498.1 |

-continued

| Compound No. | Structure | HPLC ($t_R$ in min) Method 2 | LCMS $[M + H]^+$ |
|---|---|---|---|
| 5 | 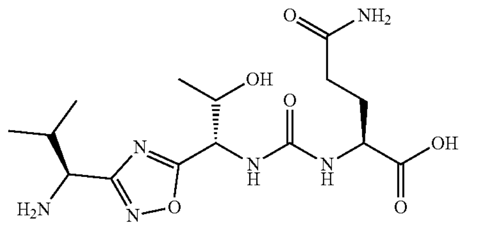 [SMILES: CC(C)[C@H](N)c1noc([C@@H](NC(=O)N[C@@H](CCC(N)=O)C(=O)O)C(C)O)n1] | 9.90 | 387.3 |
| 6 | 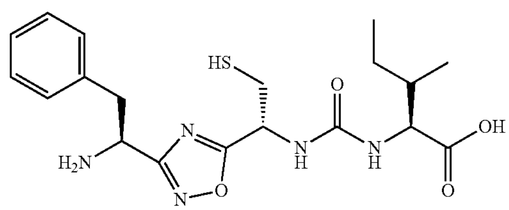 [SMILES: CCC(C)[C@H](NC(=O)N[C@@H](CS)c1nc([C@@H](N)Cc2ccccc2)no1)C(=O)O] | 14.22 | 422.0 |
| 7 | 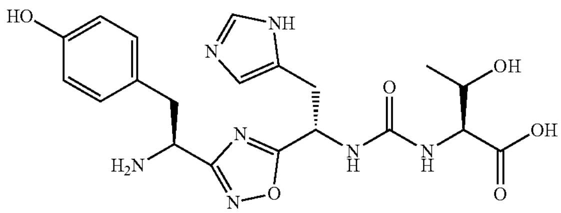 [SMILES: CC(O)[C@H](NC(=O)N[C@@H](Cc1cnc[nH]1)c1nc([C@@H](N)Cc2ccc(O)cc2)no1)C(=O)O] | 10.37 | 460.12 |
| 8 | 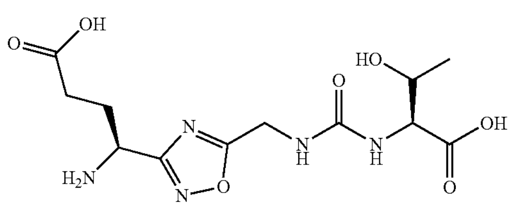 [SMILES: CC(O)[C@H](NC(=O)NCc1nc([C@@H](N)CCC(=O)O)no1)C(=O)O] | 8.86 | 346.2 |
| 9 | 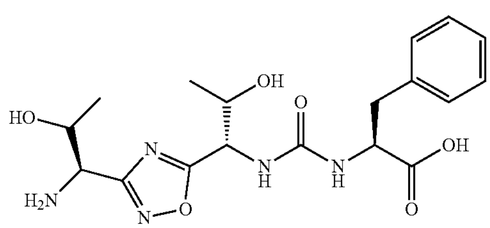 [SMILES: CC(O)[C@H](N)c1noc([C@@H](NC(=O)N[C@@H](Cc2ccccc2)C(=O)O)C(C)O)n1] | 12.06 | 408.25 |
| 10 | 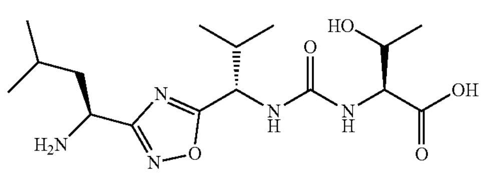 [SMILES: CC(C)C[C@H](N)c1noc([C@@H](NC(=O)N[C@H](C(=O)O)C(C)O)C(C)C)n1] | 12.51 | 372.35 |
| 11 | 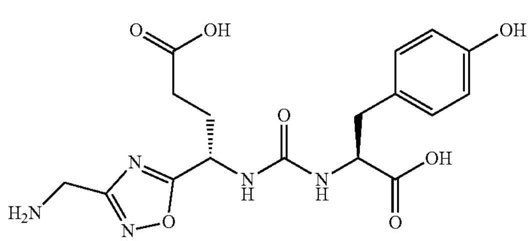 [SMILES: NCc1noc([C@H](CCC(=O)O)NC(=O)N[C@@H](Cc2ccc(O)cc2)C(=O)O)n1] | 10.71 | 408.3 |

US 12,005,045 B2

-continued

| Compound No. | Structure | HPLC ($t_R$ in min) Method 2 | LCMS [M + H]⁺ |
|---|---|---|---|
| 12 | 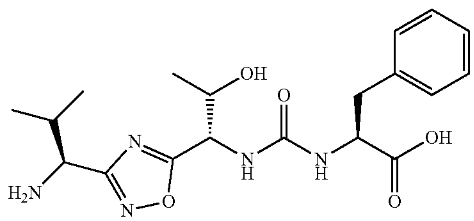 [SMILES: CC(C)[C@H](N)c1noc([C@@H](NC(=O)N[C@@H](Cc2ccccc2)C(=O)O)C(C)O)n1] | 9.52 | 406.2 |
| 13 | 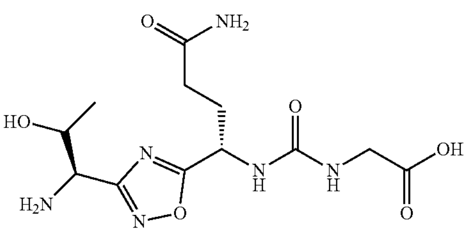 [SMILES: CC(O)[C@H](N)c1noc([C@H](CCC(N)=O)NC(=O)NCC(=O)O)n1] | 14.37 | 345.5 |

Example 2: 4-((S)-2-amino-2-(5-((S)-pyrrolidin-2-yl)-1,2,4-oxadiazol-3-yl)ethyl)phenol (Compound 14)

Step 2a: Synthesis of Compound 2a

The Compound 2a was synthesized as per the similar procedure described in steps 1a to 1c of Example 1 (Compound 1) by using Boc-Tyr(Bu)-OH.

Step 2b: Synthesis of Compound 2b

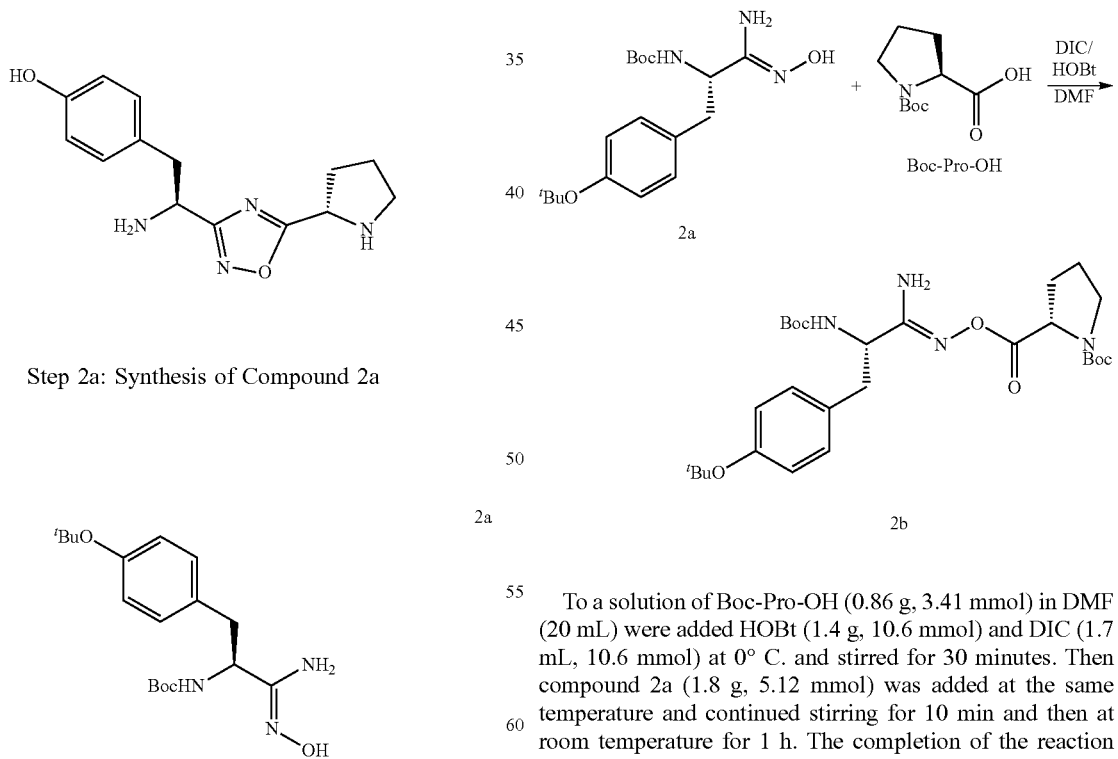

To a solution of Boc-Pro-OH (0.86 g, 3.41 mmol) in DMF (20 mL) were added HOBt (1.4 g, 10.6 mmol) and DIC (1.7 mL, 10.6 mmol) at 0° C. and stirred for 30 minutes. Then compound 2a (1.8 g, 5.12 mmol) was added at the same temperature and continued stirring for 10 min and then at room temperature for 1 h. The completion of the reaction was confirmed by TLC analysis. The reaction mixture was quenched with ice water, the precipitated white solid was filtered, washed with water and dried under high under reduced pressure. The solid was stirred with diethyl ether (50 mL) for 15 min, filtered and dried to yield 1.8 g of compound 2b. LCMS: 549.5 [M+H]⁺.

Step 2c: Synthesis of Compound 2c

Step 2d: Synthesis of Compound 14

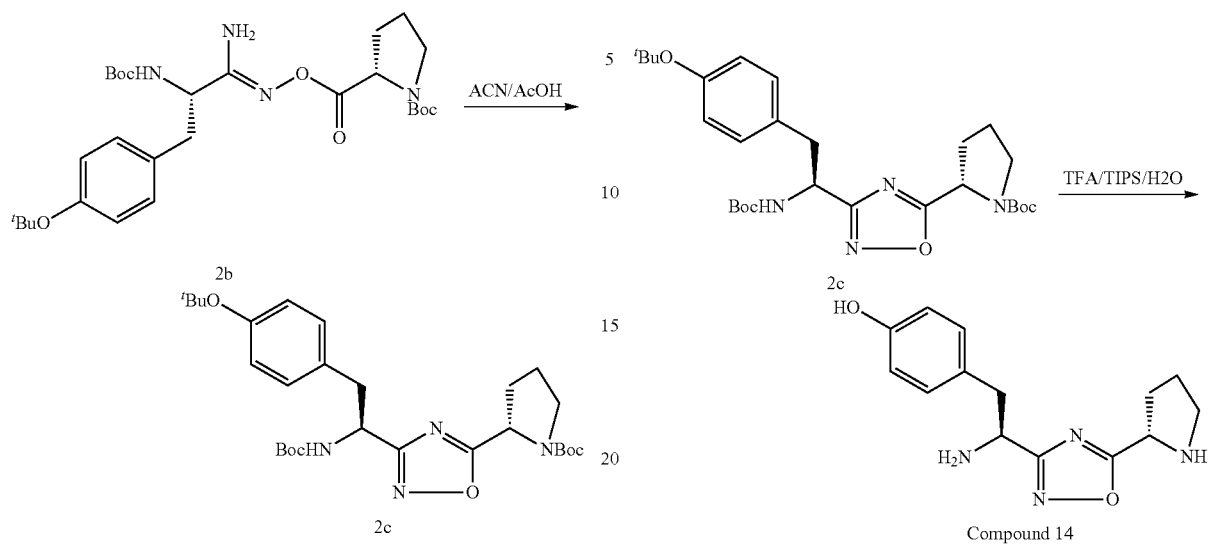

To a solution of compound 2b (1.8 g, 3.3 mmol) in acetonitrile (35 mL) was added acetic acid (1.8 mL) at room temperature and refluxed at 85° C. for 12 h. The competition of the reaction was confirmed by TLC analysis. The volatiles were evaporated under reduced pressure to obtain crude semi solid which was diluted with water and ethyl acetate. The organic layer was washed with $NaHCO_3$ solution followed by citric acid solution and brine solution. The organic layer was dried over $Na_2SO_4$, filtered and evaporated under reduced pressure to get crude. The crude compound was purified by column chromatography over silica gel using 20% ethyl acetate in hexane to yield 0.5 g compound 2c. LCMS: 531.3 $[M+H]^+$.

A solution of compound 2c (0.5 g, 0.94 mmol) was added 5 mL of cocktail mixture of and trifluoroacetic:TIPS:water (95:2.5:2.5) and was stirred at rt for 2 h. The resulting reaction mixture was evaporated under reduced pressure, diluted with diethyl ether and filtered to yield 0.45 g of crude compound 14. The crude solid material was purified by preparative HPLC method described under experimental conditions. HPLC ($t_R$ in min): 9.99; LCMS: 275.4 $[M+H]^+$.

The below compounds were prepared by procedure similar to the one described in Example 2 (Compound 14) with appropriate variations in reactants, quantities of reagents, solvents and reaction conditions. The characterization data of the compounds are summarized herein below table.

| Compound No. | Structure | HPLC ($t_R$ in min) Method 2 | LCMS $[M + H]^+$ |
|---|---|---|---|
| 15 | 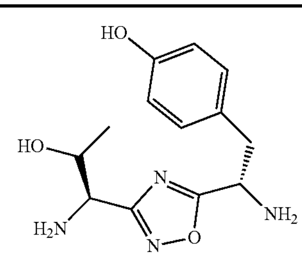 | 9.72 | 279.4 |
| 16 | 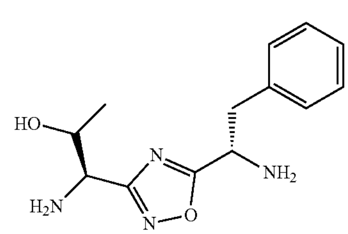 [SMILES: CC(O)[C@H](N)c1noc([C@@H](N)Cc2ccccc2)n1] | 10.79 | 263.4 |

| Compound No. | Structure | HPLC ($t_R$ in min) Method 2 | LCMS $[M + H]^+$ |
|---|---|---|---|
| 17 | 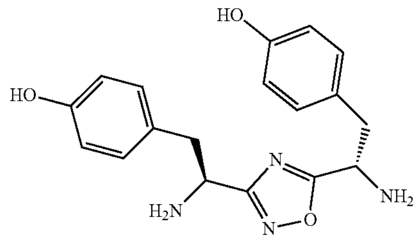 [SMILES: N[C@@H](Cc1ccc(O)cc1)c1noc([C@@H](N)Cc2ccc(O)cc2)n1] | 10.8 | 341.3 |
| 18 | 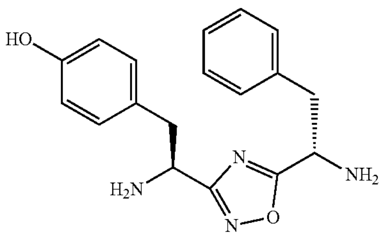 [SMILES: N[C@@H](Cc1ccc(O)cc1)c1noc([C@@H](N)Cc2ccccc2)n1] | 11.9 | 324.9 |

The synthetic procedures for the preparation of compounds 19 and 20 of the present invention were described in WO2016142833 A1.

| Compound No. | Structure |
|---|---|
| 19 | 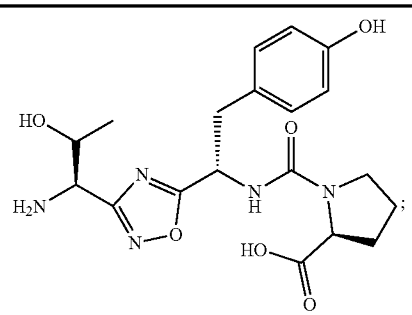 |
| 20 | 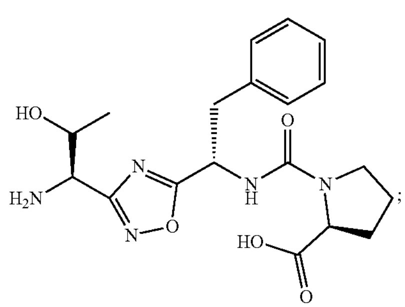 [SMILES: CC(O)[C@H](N)c1noc([C@H](Cc2ccccc2)NC(=O)N2CCC[C@H]2C(=O)O)n1] |

Example 3: Rescue of Mouse Splenocyte Proliferation in the Presence of Recombinant PD-L1/PD-L2

Recombinant mouse PD-L1 (rm-PDL-1, cat no: 1019-B7-100; R&D Systems) were used as the source of PD-L1.

Requirements:

Mouse splenocytes harvested from 6-8 weeks old C57 BL6 mice; RPMI 1640 (GIBCO, Cat #11875); DMEM with high glucose (GIBCO, Cat #D6429); Fetal Bovine Serum [Hyclone, Cat #SH30071.03]; Penicillin (10000 unit/mL)-Streptomycin (10,000 µg/mL) Liquid (GIBCO, Cat #15140-122); MEM Sodium Pyruvate solution 100 mM (100×), Liquid (GIBCO, Cat #11360); Nonessential amino acid (GIBCO, Cat #11140); L-Glutamine (GIBCO, Cat #25030); Anti-CD3 antibody (eBiosciences—16-0032); Anti-CD28 antibody (eBiosciences—16-0281); ACK lysis buffer (1 mL) (GIBCO, Cat #-A10492); Histopaque (density-1.083 gm/mL) (SIGMA 10831); Trypan blue solution (SIGMA-T8154); 2 mL Norm Ject Luer Lock syringe-(Sigma 2014-12); 40 µm nylon cell strainer (BD FALCON 35230); Hemacytometer (Bright line-SIGMA Z359629); FACS Buffer (PBS/0.1% BSA): Phosphate Buffered Saline (PBS) pH 7.2 (HiMedia TS1006) with 0.1% Bovine Serum Albumin (BSA) (SIGMA A7050) and sodium azide (SIGMA 08591); 5 mM stock solution of CFSE: CFSE stock solution was prepared by diluting lyophilized CFSE with 180 µL of Dimethyl sulfoxide (DMSO $C_2H_6SO$, SIGMA-D-5879) and aliquoted in to tubes for further use. Working concentrations were titrated from 10 µM to 1 µM. (eBioscience-650850-85); 0.05% Trypsin and 0.02% EDTA (SIGMA 59417C); 96-well format ELISA plates (Corning CLS3390); BD FACS caliber (E6016); Recombinant mouse B7-H1/PDL1 Fc Chimera, (rm-PD-L1 cat no: 1019-B7-100).

Protocol

Splenocyte Preparation and Culturing:

Splenocytes harvested in a 50 mL falcon tube by mashing mouse spleen in a 40 µm cell strainer were further treated with 1 mL ACK lysis buffer for 5 min at room temperature. After washing with 9 mL of RPMI complete media, cells were re-suspended in 3 mL of 1×PBS in a 15 mL tube. 3 mL of Histopaque was added carefully to the bottom of the tube without disturbing overlaying splenocyte suspension. After centrifuging at 800×g for 20 min at room temperature, the opaque layer of splenocytes was collected carefully without disturbing/mixing the layers. Splenocytes were washed twice with cold 1×PBS followed by total cell counting using Trypan Blue exclusion method and used further for cell based assays.

Splenocytes were cultured in RPMI complete media (RPMI+10% fetal bovine serum+1 mM sodium pyruvate+ 10,000 units/mL penicillin and 10,000 μg/mL streptomycin) and maintained in a $CO_2$ incubator with 5% $CO_2$ at 37° C.

CFSE Proliferation Assay:

CFSE is a dye that passively diffuses into cells and binds to intracellular proteins. $1 \times 10^6$ cells/mL of harvested splenocytes were treated with 5 μM of CFSE in pre-warmed 1×PBS/0.1% BSA solution for 10 min at 37° C. Excess CFSE was quenched using 5 volumes of ice-cold culture media to the cells and incubated on ice for 5 min. CFSE labelled splenocytes were further given three washes with ice cold complete RPMI media. CFSE labelled $1 \times 10^5$ splenocytes added to wells containing either MDA-MB231 cells ($1 \times 10^5$ cells cultured in high glucose DMEM medium) or recombinant human PDL-1 (100 ng/mL) and test compounds. Splenocytes were stimulated with anti-mouse CD3 and anti-mouse CD28 antibody (1 μg/mL each), and the culture was further incubated for 72 h at 37° C. with 5% $CO_2$. Cells were harvested and washed thrice with ice cold FACS buffer and % proliferation was analysed by flow cytometry with 488 nm excitation and 521 nm emission filters.

Data Compilation, Processing and Inference:

Percent splenocyte proliferation was analysed using cell quest FACS program and percent rescue of splenocyte proliferation by compound was estimated after deduction of % background proliferation value and normalising to % stimulated splenocyte proliferation (positive control) as 100%.

Stimulated splenocytes: Splenocytes+anti-CD3/CD28 stimulation

Background proliferation: Splenocytes+anti-CD3/CD28+ PD-L1

Compound proliferation: Splenocytes+anti-CD3/CD28+ PD-L1+Compound

Compound effect is examined by adding required conc. of compound to anti-CD3/CD28 stimulated splenocytes in presence of ligand (PDL-1). The results are given in the following table.

| Compound No. | Percent rescue of splenocyte proliferation at 100 nM PD-L1 based assay |
|---|---|
| 1 | 17 |
| 2 | 84 |
| 3 | 11 |
| 4 | 22 |
| 5 | 27 |
| 6 | 15 |
| 7 | 39 |
| 19 | 99 |
| 20 | 35 |

Example—4: Rescue of the Mouse CD8+ T-Cell Proliferation in the Presence of Recombinant mPVR Reagents:

96-well plates, Corning; RPMI, Cat No. R6504, Sigma; Easy Sep magnet, Cat No. 18000, Stem Cell; Easy Sep Mouse CD8 T Cell isolation kit, Cat No. 19853, Stem Cell; Corning® cell strainer, (70 μm) Cat No. 431751, Corning; Purified anti-mouse CD3 Abs, Cat No. 100201, Biolegend; Recombinant mouse PVR, Cat No. 6909-CD-050, R&D Systems; Recombinant mouse anti-TIGIT Ab, Cat No. 142101, Biolegend; FBS, Cat No. SH30070.03, Hyclone; Mouse IL-2 ELISA Kit, R&D System Cat no DY402; Mouse IFN-γ ELISA Kit R&D Systems Cat no. DY485; Sterile PBS; FicollHistopaque, Cat No. 10831-6X100ML, Sigma Protocol:

Spleen was collected from $C_{57}BL/6$ male mice with 6-8 weeks of age. Splenocytes were isolated by slowly crushing the spleen between the sterile glass slides in RPMI+10% FBS and passing it through the 70 μm strainer. Cell suspension was centrifuged at 912×g for 10 minutes at room temperature and discarded the supernatant. Splenocytes were resuspended in RPMI+10% FBS (Complete RPMI). Resuspended splenocytes were overlaid on Ficoll Histopaque-1083 in a 50 ml Tarson tubes. Overlaid cells were centrifuged at 584×g for 30 minutes at room temperature without break. A clear buffy coat was carefully aspirated into sterile PBS. Isolated cells were washed using PBS and resuspended in complete RPMI medium to get a suspension of about $5 \times 10^7$ cells/ml. Mouse CD8+ T cell were isolated by using EasySep Mouse CD8+ T Cell Isolation kit, as per manufacturers instruction.

96-well cell culture plate was coated with Purified anti-mouse CD3, 1 μg/mL (50 μL/well) and Recombinant Mouse PVR Fc Chimera, 0.5 μg/mL (50 ul/well) for 4 hours at 37° C. After 4 hours, the coated plate was washed with sterile PBS. Mouse CD8+ T cells isolated from spleen were added at 0.2 million/well (180 L) concentration into a 96-well cell culture plate. Test compound at various concentrations prepared in water or DMSO was added in respective wells (20 μL/well) so as to make the total volume 200 μL/well. The plates were incubated in 37° C. $CO_2$ incubator for 3 days. On the $3^{rd}$ day, cell supernatant was collected to determine cytokine levels (IL-2 or IFN-7) using ELISA. The extent of CD8+ T cell proliferation in presence or absence of test compound was measured by analysing the amount of IL-2 or IFN-7 in the culture supernatants using mouse IL-2 or IFN-7 ELISA kits as per manufacture instructions. Recombinant mouse anti-TIGIT antibody was used as positive control to determine the increased proliferation of CD8+ T cells.

Data Compilation, Processing and Inference:

Percent CD8+ T cell proliferation was analysed by measuring IL-2 levels using IL-2 ELISA kit and percent rescue of CD8+ T cell by test compound was estimated after deduction of % background proliferation value and normalising to % stimulated CD8+ T cell proliferation by anti-TIGIT antibody (positive control) as 100%. The results are given in following table.

| Compound No. | Percent rescue of CD8+ T-cell proliferation at 100 nM mPVR based assay |
|---|---|
| 1 | 98 |
| 2 | 14 |
| 3 | 59 |
| 5 | (17 @ 1000 nM) |
| 8 | 14.6 |
| 9 | 56.9 |
| 16 | 72 (@ 1000 nM) |
| 19 | 72 |

Example—5: Efficacy Study of Compound 19 in the CT-26 Syngeneic (Balb/c Male) Mouse Tumor Model The objective of this study was to evaluate anti-tumor activity of Compound 19 in a CT26 syngeneic colon adenocarcinoma model.

Reagents and Materials

| Name of the Reagent/ Chemical | Source | Catalogue No. |
|---|---|---|
| Media - RPMI | Sigma Aldrich | R-6504 |
| Fetal bovine serum (FBS) | Invitrogen | 10437 028 |
| Penicillin Streptomycin | Invitrogen | 15140122 |
| CT26 Cell Line | ATCC | NA |
| Anti-PD1 antibody | BioXcell | BE0033-2 |
| TIGIT antibody | BioXcell | BE027-4 |
| Tween ® 80 | Sigma Aldrich | P4780 |
| 2-Hydroxypropyl-beta-cyclodextrin HPβCD | Sigma Aldrich | 54290 |
| Citric Acid | Fisher Scientific | 22595 |
| Dipotassium EDTA salt dihydrate | Sigma Aldrich | 332593 |
| Capmul ® PG-8 NF | Abitec Corporation | Not available |

Cell Line Propagation and Inoculation

CT26 cell line was procured from ATCC, maintained and stored at ADTL-Bangalore cell line repository. One vial of CT26 cell line was thawed and revived in T-150 cm² flask with RPMI medium supplemented with 10% FBS (Gibco), 10 mM 4-(2-hydroxyethyl)-1-piperazineethanesulfonic acid (HEPES), 1 mM sodium pyruvate, 4.5 g/L Glucose, 1% penicillin streptomycin (Sigma) and 1.5 g/L sodium bicarbonate. The flask with CT26 cells at cell density 0.25 million/ml was incubated at 37±1° C. incubator supplied with 5% carbon dioxide. Cell expansion was carried out in T-150 cm² flasks and cell density was maintained between 0.25 million/flask to 1.2 million/flask, with cell splitting every alternate day. After the final step of splitting, cells were processed for injection when the cells reached exponential phase. Cells in the T-150 cm² flask were trypsinized and transferred to 50 ml tubes and centrifuged at 1200 rpm for 5 minutes at controlled room temperature to obtain cell pellet. Supernatant was discarded and cell pellets were suspended in media and counted using hemocytometer. Cell pellet was re-suspended in RPMI media at a final concentration of 10×10⁶ cells/ml. To establish tumors, 1×10⁶ cells (0.1 ml of cell suspension) were injected subcutaneously into the right flank region of mice.

Grouping and Allocation of Animals

When the mean tumor volumes reached approximately 30±5 mm³, the animals were randomized based on tumor volumes into five groups (G1 to G5) of ten animals (N=10) each as mentioned below. The treatment was continued for a period of 14 days after which the overall efficacy and tolerability were evaluated based on tumor volume and body weight changes observed during the treatment period. On treatment day 14, animals from all groups were sacrificed at 0.5 hour, 1 hour and 4 hour after last dose administration.

Grouping, Dose and Dosing Regimen (Dosing Starts after Randomization)

| Group | Compound | Dose | Frequency | Route of Administration |
|---|---|---|---|---|
| 1 | Vehicle control | 0 mg/kg | qd | Oral |
| 2 | Anti-mouse PD1 antibody | 10 µg/animal | Once weekly | I.P |
| 3 | Anti-mouse TIGIT antibody | 500 µg/animal | twice weekly | I.P |
| 4 | Compound 19 | 10 mg/kg | qd | Oral |
| 5 | Compound 19 | 30 mg/kg | qd | Oral |

There was no impact on body weight in any of the treatment in this study indicating excellent tolerability of the test agents at the dosage administered. Treatment with Compound 19 resulted in a dose dependent tumor growth inhibition (42% at 10 mg/kg (qd) and 53% at 30 mg/kg (qd) doses). Percent tumor growth inhibition observed with 30 mg/kg (qd) dose was statistically significant compared to vehicle treated animals. The result of the study is graphically represented in FIG. 1.

What is claimed:

1. A method of modulating T cell immunoreceptor with Ig and ITIM domains (TIGIT) signaling pathway and programmed cell death 1 (PD-1) signaling pathway in a subject in need thereof, comprising administering to the subject Compound 19:

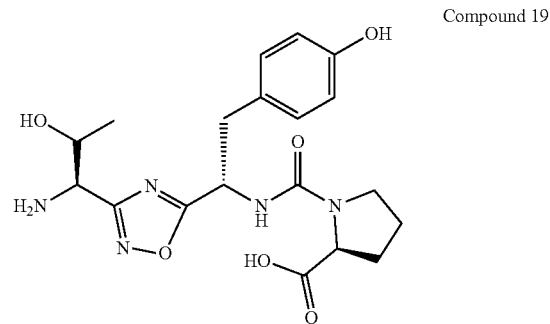 [SMILES: CC(O)[C@H](N)c1noc([C@H](Cc2ccc(O)cc2)NC(=O)N2CCC[C@H]2C(=O)O)n1]

Compound 19 or a stereoisomer thereof or a pharmaceutically acceptable salt thereof.

2. The method of claim 1, wherein the subject in need thereof is suffering from a disease or disorder selected from a cancer, immune disorder, immunodeficiency disorder, inflammatory disorder, infectious disease, transplant rejection, or combination thereof.

3. The method of claim 2, wherein the disease or disorder is a cancer.

4. The method of claim 3, wherein the cancer is selected from blastoma, breast cancer, epithelial cancer, colon cancer, lung cancer, melanoma, prostate cancer, renal cancer, bone cancer, pancreatic cancer, skin cancer, cancer of the head or neck, uterine cancer, ovarian cancer, colorectal cancer, rectal cancer, cancer of the anal region, cancer of the peritoneum, stomach cancer, testicular cancer, carcinoma of the fallopian tubes, carcinoma of the endometrium, cervical cancer, vaginal cancer, vulval cancer, cancer of the esophagus, cancer of the small intestine, cancer of the endocrine system, cancer of the thyroid gland, cancer of the parathyroid gland, cancer of the adrenal gland, sarcoma, cancer of the urethra, cancer of the penis, chronic or acute leukemia, solid tumors of childhood, Hodgkin's lymphoma, non-Hodgkin's lymphoma, cutaneous T cell lymphoma, mesothelioma, thymic carcinoma, myeloma, cancer of the bladder, cancer of the ureter, carcinoma of the renal pelvis, liver cancer, pancreatic cancer, post-transplant lymphoproliferative disorder (PTLD), neoplasm of the central nervous system (CNS), tumor angiogenesis, spinal axis tumor, brain stem glioma, pituitary adenoma, epidermoid cancer, salivary gland carcinoma, squamous cell cancer, abnormal vascular proliferation associated with phakomatoses, edema (such as that associated with brain tumors), Meigs' syndrome, Merkel cell carcinoma, and an environmentally induced cancer.

5. The method of claim 2, wherein the disease is an infectious disease.

6. The method of claim 5, wherein the infectious disease is a bacterial infection, a viral infection, a fungal infection, or a parasitic infection.

7. A method of treating a disease or disorder mediated by both TIGIT signalling pathway and PD-1 signalling pathway in a subject in need thereof, the method comprising administering to the subject a therapeutically effective amount of Compound 19:

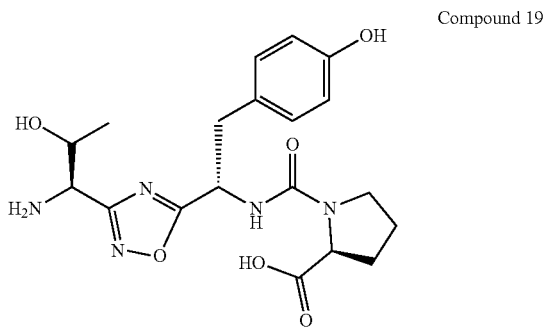 [SMILES: CC(O)[C@H](N)c1noc([C@H](Cc2ccc(O)cc2)NC(=O)N2CCC[C@H]2C(=O)O)n1]

Compound 19 or a stereoisomer thereof or a pharmaceutically acceptable salt thereof.

8. The method of claim 7, wherein the disease or disorder is a cancer, immune disorder, immunodeficiency disorder, inflammatory disorder, infectious disease, transplant rejection, or combination thereof.

9. The method of claim 8, wherein the cancer is selected from blastoma, breast cancer, epithelial cancer, colon cancer, lung cancer, melanoma, prostate cancer, renal cancer, bone cancer, pancreatic cancer, skin cancer, cancer of the head or neck, uterine cancer, ovarian cancer, colorectal cancer, rectal cancer, cancer of the anal region, cancer of the peritoneum, stomach cancer, testicular cancer, carcinoma of the fallopian tubes, carcinoma of the endometrium, cervical cancer, vaginal cancer, vulval cancer, cancer of the esophagus, cancer of the small intestine, cancer of the endocrine system, cancer of the thyroid gland, cancer of the parathyroid gland, cancer of the adrenal gland, sarcoma, cancer of the urethra, cancer of the penis, chronic or acute leukemia, solid tumors of childhood, Hodgkin's lymphoma, non-Hodgkin's lymphoma, cutaneous T cell lymphoma, mesothelioma, thymic carcinoma, myeloma, cancer of the bladder, cancer of the ureter, carcinoma of the renal pelvis, liver cancer, pancreatic cancer, post-transplant lymphoproliferative disorder (PTLD), neoplasm of the central nervous system (CNS), tumor angiogenesis, spinal axis tumor, brain stem glioma, pituitary adenoma, epidermoid cancer, salivary gland carcinoma, squamous cell cancer, abnormal vascular proliferation associated with phakomatoses, edema (such as that associated with brain tumors), Meigs' syndrome, Merkel cell carcinoma, and an environmentally induced cancer.

10. The method of claim 8, wherein the infectious disease is a bacterial infection, a viral infection, a fungal infection, or a parasitic infection.

11. A method of modulating T cell immunoreceptor with Ig and ITIM domains (TIGIT) signaling pathway in a subject in need thereof, comprising administering to the subject Compound 19:

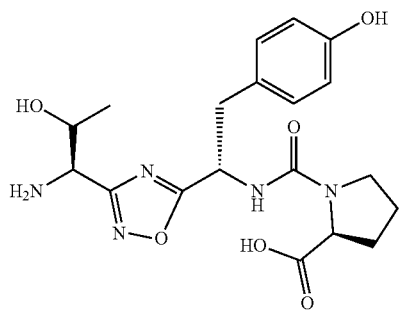

Compound 19 or a stereoisomer thereof or a pharmaceutically acceptable salt thereof.

12. The method of claim 11, wherein the method further comprises modulating the PD-1 signalling pathway.

13. The method of claim 11, wherein the subject in need thereof is suffering from a disease or disorder selected from a cancer, immune disorder, immunodeficiency disorder, inflammatory disorder, infectious disease, transplant rejection, or combination thereof.

14. The method of claim 11, wherein the modulating is inhibiting growth of tumor cells and/or metastasis.

15. The method of claim 14, wherein the tumor cells are of a cancer selected from small cell lung cancer, multiple myeloma, bladder carcinoma, primary ductal carcinoma, ovarian carcinoma, Hodgkin's lymphoma, gastric carcinoma, acute myeloid leukemia, and pancreatic cancer.

16. A method of treating a disease or disorder mediated by TIGIT signalling pathway in a subject in need thereof, the method comprising administering to the subject a therapeutically effective amount of Compound 19:

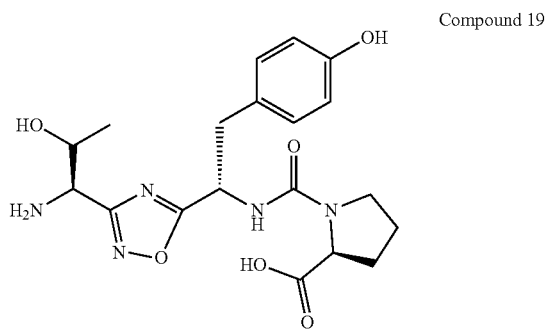 [SMILES: CC(O)[C@H](N)c1noc([C@H](Cc2ccc(O)cc2)NC(=O)N2CCC[C@H]2C(=O)O)n1]

Compound 19 or a stereoisomer thereof or a pharmaceutically acceptable salt thereof.

17. The method of claim 16, wherein the disease or disorder is a cancer, immune disorder, immunodeficiency disorder, inflammatory disorder, infectious disease, transplant rejection, or combination thereof.

18. The method of claim 17, wherein the cancer is selected from blastoma, breast cancer, epithelial cancer, colon cancer, lung cancer, melanoma, prostate cancer, renal cancer, bone cancer, pancreatic cancer, skin cancer, cancer of the head or neck, uterine cancer, ovarian cancer, colorectal cancer, rectal cancer, cancer of the anal region, cancer of the peritoneum, stomach cancer, testicular cancer, carcinoma of the fallopian tubes, carcinoma of the endometrium, cervical cancer, vaginal cancer, vulval cancer, cancer of the esophagus, cancer of the small intestine, cancer of the endocrine system, cancer of the thyroid gland, cancer of the parathyroid gland, cancer of the adrenal gland, sarcoma, cancer of the urethra, cancer of the penis, chronic or acute leukemia, solid tumors of childhood, Hodgkin's lymphoma, non-Hodgkin's lymphoma, cutaneous T cell lymphoma, mesothelioma, thymic carcinoma, myeloma, cancer of the bladder, cancer of the ureter, carcinoma of the renal pelvis, liver cancer, pancreatic cancer, post-transplant lymphoproliferative disorder (PTLD), neoplasm of the central nervous system (CNS), tumor angiogenesis, spinal axis tumor, brain stem glioma, pituitary adenoma, epidermoid cancer, salivary gland carcinoma, squamous cell cancer, abnormal vascular proliferation associated with phakomatoses, edema (such as that associated with brain tumors), Meigs' syndrome, Merkel cell carcinoma, and an environmentally induced cancer.

19. The method of claim 17, wherein the infectious disease is a bacterial infection, a viral infection, a fungal infection, or a parasitic infection.

\* \* \* \* \*